(12) United States Patent
Davis

(10) Patent No.: US 12,371,700 B2
(45) Date of Patent: Jul. 29, 2025

(54) INTERGENIC SEQUENCE REGIONS AND USES THEREOF

(71) Applicant: Monsanto Technology LLC, St. Louis, MO (US)

(72) Inventor: Ian W. Davis, Grover, MO (US)

(73) Assignee: Monsanto Technology LLC, St. Louis, MO (US)

( * ) Notice: Subject to any disclaimer, the term of this patent is extended or adjusted under 35 U.S.C. 154(b) by 928 days.

(21) Appl. No.: 17/512,614

(22) Filed: Oct. 27, 2021

(65) Prior Publication Data

US 2022/0154196 A1    May 19, 2022

Related U.S. Application Data

(62) Division of application No. 16/921,495, filed on Jul. 6, 2020, now Pat. No. 11,225,669.

(60) Provisional application No. 62/875,752, filed on Jul. 18, 2019.

(51) Int. Cl.
*C12N 15/82* (2006.01)

(52) U.S. Cl.
CPC ................ *C12N 15/8216* (2013.01)

(58) Field of Classification Search
None
See application file for complete search history.

(56) References Cited

U.S. PATENT DOCUMENTS

| 11,225,669 B2 * | 1/2022 | Davis ............ C12N 15/8216 |
| 2008/0216201 A1 | 9/2008 | Yi et al. |
| 2009/0222947 A1 | 9/2009 | Zieler et al. |
| 2014/0329326 A1 | 11/2014 | Mirsky et al. |
| 2017/0342426 A1 | 11/2017 | Armstrong et al. |
| 2018/0051295 A1 | 2/2018 | Allen et al. |

OTHER PUBLICATIONS

Gudynaite-Savitch et al. (2009) Plant Biotech J 7:742-85.*
Kurbidaeva & Purugganan (2021) "Insulators in Plants: Progress and Open Questions" Genes 12(9):1422.*
Collier et al., A versatile and robust Agrobacterium-based gene slacking system generates high-quality transgenic *Arabidopsis* plants, Plant J. 95:573-583, 2018.
GenBank Accession No. CP011421.1, Klebsiella pneumoniae strain yzusk-4 genome; the region between nucleotides 3164496 and 3163459, 2015.
International Search Report and Written Opinion for International Appl. No. PCT/US2020/040883, dated Dec. 30, 2020.
Lampropoulos et al., GreenGate—A novel, versatile, and efficient cloning system for plant transgenesis, PLoS One 8(12):e83043, 2013.
Gudynaite-Savitch et al., "Strategies to mitigate transgene-promoter interactions." Plant Biotechnology Journal, 2009, 7: 472-485.
European Search Report and Written Opinion regarding European App. No. 20841320.3, dated Jul. 24, 2023.

* cited by examiner

*Primary Examiner* — Russell T Boggs
(74) *Attorney, Agent, or Firm* — Dentons US LLP; Judith Koehler

(57) ABSTRACT

The invention provides recombinant DNA molecules comprising novel synthetic Intergenic Sequence Regions for use in plants to reduce the interaction of a first transgene expression cassette on a second transgene cassette when inserted between the first transgene cassette and second transgene cassette. The invention also provides transgenic plants, plant cells, plant parts, and seeds comprising the novel synthetic Intergenic Sequence Regions. The invention also provides methods to reduce the interaction between transgene expression cassettes using the novel synthetic Intergenic Sequence Regions.

15 Claims, 2 Drawing Sheets

Specification includes a Sequence Listing.

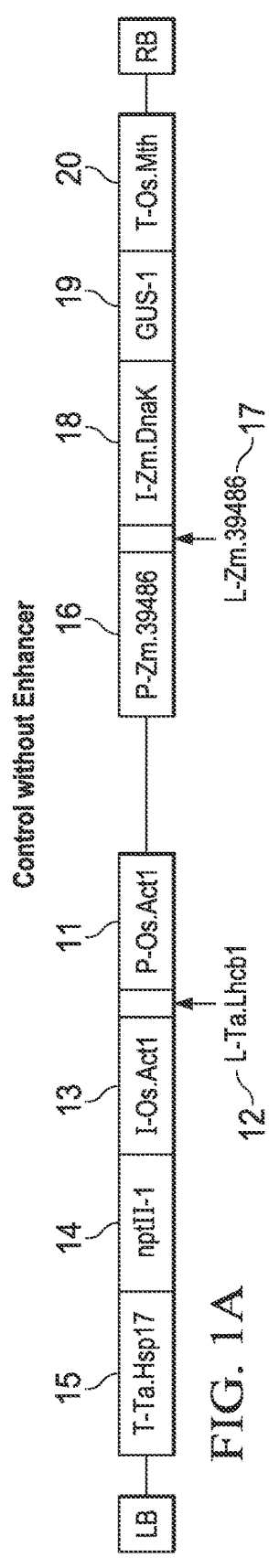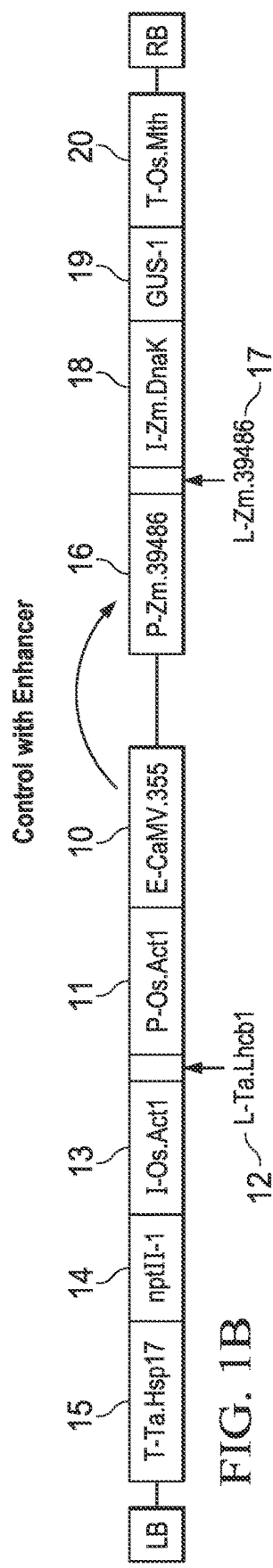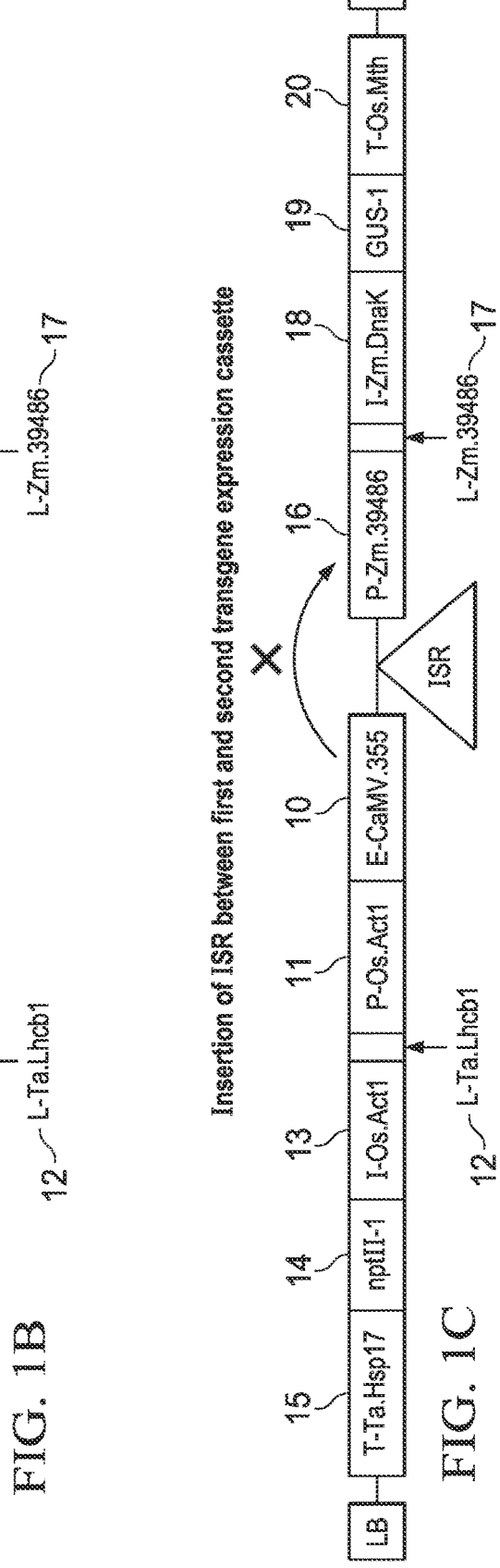

INTERGENIC SEQUENCE REGIONS AND USES THEREOF

REFERENCE TO RELATED APPLICATIONS

This application is a divisional of U.S. patent application Ser. No. 16/921,495, filed Jul. 6, 2020, which claims the benefit of priority to U.S. Provisional Application No. 62/875,752, filed Jul. 18, 2019, each of the disclosures of which are incorporated herein by reference in their entirety.

INCORPORATION OF SEQUENCE LISTING

The file named "MONS472US_ST25.txt" containing a computer-readable form of the Sequence Listing was created on Jun. 9, 2020. This file is 38,698 bytes (measured in MS-Windows®), is contemporaneously filed by electronic submission (using the United States Patent Office EFS-Web filing system), and is incorporated into this application by reference in its entirety.

FIELD OF THE INVENTION

The invention relates to the field of plant molecular biology and plant genetic engineering. More specifically, the invention relates to DNA molecules useful for reducing the influence of one transgene cassette on the expression of another transgene cassette in plants.

BACKGROUND OF THE INVENTION

Intergenic Sequence Regions ("ISRs") are DNA sequences that, when placed between two or more transgene cassettes, reduce the interaction of one transgene cassette on another transgene cassette, preventing the alteration of the expression pattern of transgene cassettes due to expression element interaction between cassettes.

Expression elements in an expression cassette such as promoters, introns, and 3' untranslated regions (3' UTRs) contain cis-acting elements that have the potential to influence expression of an adjacent or neighboring expression cassette. For example, a plant viral promoter such as that of the Cauliflower Mosaic Virus 35S promoter (CaMV 35S) is comprised of enhancer domains that can influence the transcription of nearby genes, activating genes up to 4.3 Kb upstream or downstream from the site of insertion (Gudynaile- Savitch et al. (2009) *Strategies to mitigate transgene-promoter interactions. Plant Biotechnology Journal,* 7: 472-485; Benfey et al. (1990) *Tissue-specific expression from CaMV 35S enhancer subdomains in early stages of plant development. The EMBO Journal,* 9:1677-1684). For example, in one instance a transgene cassette subcloned into a plant transformation vector comprising a selection cassette using the CaMV 35S promoter to drive a selectable marker coding sequence was affected by the presence of the CaMV 35S promoter, which altered the tissue-specific expression of the transgene cassette to a more constitutive pattern (Yoo et al. (2005) *The 35S promoter used in a selectable marker gene of a plant transformation vector affects the expression of the transgene. Planta,* 221: 523-530).

Increasingly, in the field of plant biotechnology, vectors comprising multiple transgene cassettes are being used to transform plants to introduce several agronomically important characteristics in a single vector stack. The advantage to this process is that several agronomic traits can be comprised in a single genetic locus, allowing for a more efficient and less costly breeding process when breeding the vector stacked plant with another transgenic plant comprising additional agronomic characteristics. However, as more expression cassettes are cloned into a vector, there is the potential for expression elements from one expression cassette to alter or influence the expression profile of another expression cassette in the vector stack. An expression cassette designed to provide a specific pattern of tissue expression, such as expression in the seed, may change expression as a result of the interaction between the expression elements of a neighboring expression cassette in the vector stack, altering the seed-specific expression pattern to one more closely resembling the neighboring expression cassette. This can negatively affect the intended phenotype of the seed-specific expression cassette. Therefore, there is a need in plant biotechnology for DNA sequences that can reduce or prevent the interaction of adjacent and neighboring expression cassettes in a vector stack.

Thus, the inventor discloses herein novel synthetic ISRs that minimize the interaction of expression cassettes in a vector stack in transgenic plants. These ISRs can be placed between adjacent expression cassettes in a single vector stack to prevent interaction between the expression elements of individual cassettes, thus maintaining the intended expression pattern and level of expression of each expression cassette within the vector stack.

SUMMARY OF THE INVENTION

The invention provides novel synthetic Intergenic Sequence Regions or ISRs for use in plants. The invention also provides recombinant DNA constructs comprising the ISRs. The present invention also provides transgenic plant cells, plants, and seeds comprising the ISRs. In one embodiment, the ISRs are inserted between expression cassettes in a vector stack. The present invention also provides methods for using the ISRs and making and using the recombinant DNA constructs comprising the ISRs, and the transgenic plant cells, plants, and seeds comprising the ISRs.

Thus, in one aspect, the invention provides a recombinant DNA molecule comprising a DNA sequence selected from the group consisting of: (a) a sequence with at least 85 percent sequence identity to any of SEQ ID NOs:1-6; and (b) a sequence comprising any of SEQ ID NOs:1-6. In specific embodiments, the recombinant DNA molecule comprises a DNA sequence having at least about 85 percent, at least about 86 percent, at least about 87 percent, at least about 88 percent, at least about 89 percent, at least about 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs:1-6.

In another aspect, provided herein are transgenic plant cells comprising recombinant DNA molecule comprising a DNA sequence selected from the group consisting of: (a) a sequence with at least 85 percent sequence identity to any of SEQ ID NOs:1-6; and (b) a sequence comprising any of SEQ ID NOs:1-6. In certain embodiments, the transgenic plant cell is a monocotyledonous plant cell. In other embodiments, the transgenic plant cell is a monocotyledonous plant cell or a dicotyledonous plant cell.

In still yet another aspect, further provided herein is a transgenic plant, or part thereof, comprising a recombinant DNA molecule comprising a DNA sequence selected from the group consisting of: (a) a sequence with at least 85 percent sequence identity to any of SEQ ID NOs:1-6; and (b) a sequence comprising any of SEQ ID NOs:1-6. In specific embodiments, the transgenic plant is a progeny plant of any generation that comprises the recombinant DNA molecule. A transgenic seed comprising the recombinant DNA molecule that produces such a transgenic plant when grown is also provided herein.

In another aspect, the invention provides a method of producing a commodity product comprising obtaining a transgenic plant or part thereof containing a recombinant DNA molecule of the invention and producing the commodity product therefrom. In one embodiment, the commodity product is seeds, processed seeds, protein concentrate, protein isolate, starch, grains, plant parts, seed oil, biomass, flour and meal.

In still yet another aspect, the invention provides a method for reducing the interaction of a first transgene expression cassette with a second transgene expression cassette within a transgenic plant transformed with a vector stack, said method comprising transforming a plant cell with a vector stack comprising a recombinant DNA molecule comprising: (a) a first transgene cassette; (b) a second transgene cassette: (c) a DNA molecule comprising a sequence selected from the group consisting of: (i) a sequence with at least 85 percent sequence identity to any of SEQ ID NOs:1-6; and (ii) a sequence comprising any of SEQ ID NOs:1-6; wherein the DNA molecule is inserted between the first transgene expression cassette and the second transgene expression cassette; and (d) regenerating a transgenic plant from the transformed plant cell. In certain embodiments, the vector stack is comprised of more than two expression cassettes. In further embodiments, the DNA molecule of any of SEQ ID NOs:1-6 are inserted between each of the expression cassettes within the vector stack.

BRIEF DESCRIPTION OF THE SEQUENCES

SEQ ID NO:1 is a DNA sequence of Intergenic Sequence Region ISR4_Stop which comprises the ISR4 (SEQ ID NO:4) and three stop codons on both the 5' and 3' ends.

SEQ ID NO:2 is a DNA sequence of Intergenic Sequence Region ISR89.

SEQ ID NO:3 is a DNA sequence of Intergenic Sequence Region ISR2.

SEQ ID NO:4 is a DNA sequence of Intergenic Sequence Region ISR4.

SEQ ID NO:5 is a DNA sequence of Intergenic Sequence Region ISR97.

SEQ ID NO:6 is a DNA sequence of Intergenic Sequence Region ISR69

SEQ ID NO:7 is a DNA sequence of Intergenic Sequence Region ISR88.

SEQ ID NO:8 is a DNA sequence of Intergenic Sequence Region ISR86.

SEQ ID NO:9 is a DNA sequence of Intergenic Sequence Region ISR_X.

SEQ ID NO:10 is a DNA sequence of an enhancer. E-CaMV.35S.2xA1-B3-1:1:1, presented in FIGS. 1a-c as "E-CaMV.35S."

SEQ ID NO:11 is a DNA sequence of a promoter, P-Os.Act1:67, presented in FIGS. 1a-c as "P-Os.Act1."

SEQ ID NO:12 is a DNA sequence of a leader or 5' UTR, L-Ta.Lhcb1:1, presented in FIGS. 1a-c as "L-Ta.Lhcb1."

SEQ ID NO:13 is a DNA sequence of an intron. I-Os-.Act1-1:1:19, presented in FIGS. 1a-c as "I-Os.Act1."

SEQ ID NO:14 is a DNA sequence encoding neomycin phosphotransferase, CR-Ec.nptII-Tn5-1:1:3, presented in FIGS. 1a-c as "nptII-1."

SEQ ID NO:15 is a DNA sequence of a 3' UTR, T-Ta.Hsp17-1:1:1, presented in FIGS. 1a-c as "T-Ta.Hsp17."

SEQ ID NO:16 is a DNA sequence of a promoter, P-Zm.39486-1:1:1, presented in FIGS. 1a-c as "P-Zm.39486."

SEQ ID NO:17 is a DNA sequence of leader or 5' UTR, L-Zm.39486-1:1:1, presented in FIGS. 1a-c as "L-Zm.39486."

SEQ ID NO:18 is a DNA sequence of an intron, I-Zm.DnaK:1, presented in FIGS. 1a-c as "I-Zm.DnaK."

SEQ ID NO:19 is a DNA sequence of synthetic coding sequence optimized for plant expression for β-glucuronidase (GUS-1: GOI-Ec.uidA+St.LS1.nno:1) with a processable intron derived from the potato light-inducible tissue-specific ST-LS1 gene (Genbank Accession: X04753), presented in FIGS. 1a-c as "GUS-1."

SEQ ID NO:20 is a DNA sequence of a 3' UTR. T-Os.Mth-1:1:1, presented in FIGS. 1a-c as "T-Os.Mth."

SEQ ID NO:21 is a DNA sequence of a promoter, P-FMV.35S-enh-1:1:2, presented in FIGS. 2a-c as "P-FMV.35S."

SEQ ID NO:22 is a DNA sequence of a leader or 5' UTR, L-Ph.DnaK-1:1:3, presented in FIGS. 2a-c as "L-Ph.DnaK."

SEQ ID NO:23 is a DNA sequence encoding neomycin phosphotransferase, CR-Ec.nptII-Tn5-1:1:2, presented in FIGS. 2a-c as "nptII-2."

SEQ ID NO:24 is a DNA sequence of a 3' UTR, T-Mt.AC139600v16:1, presented in FIGS. 2a-c as "T-AC139600."

SEQ ID NO:25 is a DNA sequence of a promoter, P-Gm.Sphas1:14, presented in FIGS. 2a-c as "P-Gm.Sphas."

SEQ ID NO:26 is a DNA sequence of a leader or 5' UTR, L-Gm.Sphas1-1:1:1, presented in FIGS. 2a-c as "L-Gm.Sphas."

SEQ ID NO:27 is a DNA sequence of synthetic coding sequence for β-glucuronidase (GUS-2: GOI-GUS:1:2) with a processable intron derived from the potato light-inducible tissue-specific ST-LS1 gene (Genbank Accession: X04753), presented in FIGS. 2a-c as "GUS-2."

SEQ ID NO:28 is a DNA sequence of a 3' UTR, T-Mt.AC145767v28:3, presented in FIGS. 2a-c as "T-AC145767."

BRIEF DESCRIPTION OF THE DRAWINGS

FIGS. 1a-c are diagrammatic representations of vector stacks used to assay the effectiveness of synthetic Intergenic Sequence Regions ("ISRs") in reducing the interaction of two transgene expression cassettes in a single vector stack on each other's expression in stably transformed corn plants. The reference numbers in the figures indicate the corresponding sequence identifier for each genetic element as presented in the Brief Description of the Sequences. FIG. 1a shows the transgene expression cassette configuration for a control vector stack. Control without Enhancer. The Control without Enhancer is comprised of two transgene expression cassettes cloned in divergent orientation. A first transgene cassette is comprised of a promoter, P-Os.Act1:67 (SEQ ID NO:11), operably linked 5' to a leader, L-Ta.Lhcb1:1 (SEQ ID NO:12), operably linked 5' to an intron, I-Os.Act1-1:1:19 (SEQ ID NO:13), operably linked 5' to a coding sequence for neomycin phosphotransferase, CR-Ec.nptII-Tn5-1:1:3 (SEQ ID NO:14), operably linked 5' to a 3' UTR, T-Ta.Hsp17-1:1:1 (SEQ ID NO:15). A second transgene cassette, cloned in a divergent direction relative to the first transgene cassette, is comprised of a seed-specific promoter, P-Zm.39486-1:1:1 (SEQ ID NO:16), operably linked 5' to a leader, L-Zm.39486-1:1:1 (SEQ ID NO:17), operably linked 5' to an intron, I-Zm.DnaK:1 (SEQ ID NO:18), operably linked 5' to a coding sequence encoding GUS-1, GOI-Ec.uidA+St.LS1.nno:1 (SEQ ID NO:19), operably linked 5' to a 3' UTR. T-Os.Mth-1:1:1 (SEQ ID NO:20). FIG. 1b shows the transgene expression cassette configuration for a control vector stack. Control with Enhancer. The Control with Enhancer is comprised of a strong enhancer. E-CaMV.35S.2xA1-B3-1:1:1 (SEQ ID NO:10) comprising tandem repeats of specific enhancer regions derived from the Cauliflower mosaic virus 35S promoter, operably linked 5' to a promoter, P-Os.Act1:67 (SEQ ID NO:11), operably linked 5' to a leader, L-Ta.Lhcb1:1 (SEQ ID NO:12), operably linked 5' to an intron. I-Os.Act1-1:1:19 (SEQ ID NO:13), operably linked 5' to a coding sequence for neomycin phosphotransferase. CR-Ec.nptII-Tn5-1:1:3 (SEQ ID NO:14), operably linked 5' to a 3' UTR, T-Ta.Hsp17-1:1:1 (SEQ ID NO:15). A second transgene cassette, cloned in a divergent direction relative to the first transgene cassette is comprised of a seed-specific promoter, P-Zm.39486-1:1:1 (SEQ ID NO:16), operably linked 5' to a leader, L-Zm.39486-1:1:1 (SEQ ID NO:17), operably linked 5' to an intron, I-Zm.DnaK:1 (SEQ ID NO:18), operably linked 5' to a coding sequence encoding GUS-1, GOI-Ec.uidA+ St.LS1.nno:1 (SEQ ID NO:19), operably linked 5' to a 3' UTR, T-Os.Mth-1:1:1 (SEQ ID NO:20). The Control with Enhancer in FIG. 1a lacks an ISR between the first and second transgene expression cassettes. As a result, the enhancer from the first transgene expression cassette interacts with and alters the expression of the seed-specific promoter in the second transgene expression cassette, changing the expression of the second expression transgene cassette from seed-specific to constitutive. In FIG. 1c, an ISR is cloned between the first and second transgene expression cassettes of the Control with Enhancer. If the ISR is effective, then it will reduce the interaction of the enhancer in the first transgene expression cassette on the expression of the promoter in the second expression transgene cassette, reducing expression in non-seed tissues relative to the Control with Enhancer.

FIG. 2a shows the transgene expression cassette configuration for a control vector stack. Control without Enhancer. The Control without Enhancer (FIG. 2a) is comprised of a seed-specific promoter, P-Gm.Sphas1:14 (SEQ ID NO:25), operably linked 5' to a leader, L-Gm.Sphas1-1:1:1 (SEQ ID NO:26), operably linked 5' to a coding sequence encoding GUS-2, GOI-GUS:1:2 (SEQ ID NO:27), operably linked 5' to a 3' UTR, T-Mt.AC145767v28:3 (SEQ ID NO:28). The seed-specific promoter is able to drive GUS expression primarily in the seed of the soybean plant in the Control without Enhancer. FIG. 2b shows the transgene expression cassette configuration for a control vector stack, Control with Enhancer. The Control with Enhancer is comprised of two transgene expression cassettes in divergent orientation. A first transgene cassette is comprised of a strong promoter derived from the Figwort mosaic virus 35S promoter with a rearranged and duplicated enhancer, P-FMV.35S-enh-1:1:2 (SEQ ID NO:21), operably linked 5' to a leader, L-Ph.DnaK-1:1:3 (SEQ ID NO:22), operably linked 5' to a coding sequence for neomycin phosphotransferase. CR-Ec.nptII-Tn5-1:1:2 (SEQ ID NO:23), operably linked 5' to a 3' UTR, T-Mt.AC139600v16:1 (SEQ ID NO:24). A second transgene cassette, cloned in a divergent direction relative to the first transgene cassette is comprised of a seed-specific promoter, P-Gm.Sphas1:14 (SEQ ID NO:25), operably linked 5' to a leader, L-Gm.Sphas1-1:1:1 (SEQ ID NO:26), operably linked 5' to a coding sequence encoding GUS-2. GOI-GUS:1:2 (SEQ ID NO:27), operably linked 5' to a 3' UTR, T-Mt.AC145767v28:3 (SEQ ID NO:28). The Control with Enhancer lacks an ISR between the first and second transgene expression cassette. As a result, the seed-specific promoter expression in the second transgene expression cassette is affected by the enhancer region of the Figwort mosaic virus 35S promoter in the first transgene expression cassette, changing the expression of the second expression transgene cassette from seed-specific to constitutive. In FIG. 2c, an ISR is cloned between the first and second transgene expression cassette of the Control with Enhancer. If the ISR is effective, then it will reduce the interaction of the enhancer region of the Figwort mosaic virus 35S promoter in the first transgene expression cassette with the promoter in the second transgene expression cassette, reducing expression in non-seed tissues relative to the Control with Enhancer.

DETAILED DESCRIPTION OF THE INVENTION

Figure 2A:
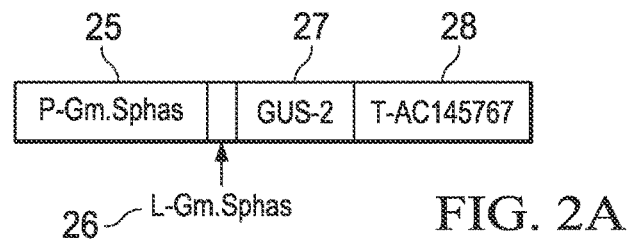
FIGS. 2a-c are a diagrammatic representation of vector stacks used to assay the effectiveness of ISRs in reducing the interaction of two transgene expression cassettes in a single vector stack on each other's expression in stably transformed soy plants. The reference numbers in the figures indicate the corresponding sequence identifier for each genetic element as presented in the Brief Description of the Sequences.

The invention provides novel synthetic Intergenic Sequence Regions ("ISRs") for use in transgenic plants. The nucleotide sequences of these novel synthetic ISRs are provided as SEQ ID NOs:1-6. These synthetic ISRs reduce the interaction of expression elements in a first transgene expression cassette on the expression of a second transgene cassette in a transgenic plant when inserted between the first transgene expression cassette and second transgene. The invention also provides transgenic plant cells, plants, and seeds comprising the ISRs. The invention also provides methods for using the ISRs and making and using the recombinant DNA molecules comprising the ISRs.

The following definitions and methods are provided to better define the present invention and to guide those of ordinary skill in the art in the practice of the present invention. Unless otherwise noted, terms are to be understood according to conventional usage by those of ordinary skill in the relevant art.

ISRs and the Interaction of a First Transgene Expression Cassette with a Second Transgene Expression Cassette As used herein, the term "interaction" refers to the effect of one or more elements in a first transgene expression cassette on the expression pattern of a second transgene expression cassette when provided in close proximity to each other in a transgenic plant, in certain embodiments having been transformed using a vector stack.

The regulatory elements within each transgene expression cassette are comprised of various cis-elements that are bound by trans-acting factors which effect transcription of a transgene. For example, a plant promoter is comprised of cis-elements that are essential for the initiation of transcription and efficiency of transcription. In addition, a plant promoter is often comprised of other cis-element motifs that can modulate transcription in response to a particular stimulus such as stress (ABRE and AB14), pathogen (W Box), or light (GT1-motif). Other cis-elements can provide tissue-specific or tissue-preferred expression (Porto et al. (2014)

Plant Promoters: An Approach of Structure and Function. Mol. Biotechnol 56: 38-49). For example, the Cauliflower mosaic virus 35S promoter comprises an enhancer region made of two domains. The downstream domain, domain A, confers expression principally in the roots. A cis-element within a twenty-two base pair region within Domain A, as-1 is primarily responsible for this expression. The upstream domain, domain B, confers expression in most cell types of leaf and stem as well as in vascular tissue of the roots (Benfey et al. (1990) *Tissue-specific expression from CaMV 35S enhancer subdomains in early stages of plant development. The EMBO Journal,* 9:1677-1684).

When two transgene expression cassettes are adjacent to each other in the plant genome, there is the potential for the expression elements of one transgene expression cassette to alter the expression of the other transgene expression cassette. This "interaction" of one transgene expression cassette with an adjacent transgene expression cassette in transgenic plants is demonstrated in Examples 2 and 3 by the Control with Enhancer.

"Leakiness" is the term used to describe the level of average expression change in tissues caused by the interaction of expression elements in a first expression cassette on the expression profile of a second expression cassette. Leakiness is determined by comparing the expression profile of a Control with Enhancer to the expression profile of the test vector stack with an ISR (which is comprised of the Control with Enhancer with an ISR inserted between the two transgene cassettes). The leakiness of the Control without Enhancer compared to the Control with Enhancer is 100%. Leakiness of the constructs comprising an ISR is determined by dividing the average GUS expression in the non-target tissues in the test construct by the average GUS expression in the non-target tissues of the Control with Enhancer construct and multiplying by one-hundred. The percent reduction in leakiness is determined by subtracting the percent leakiness from one-hundred percent.

"Intergenic Sequence Region" or "ISR" is a synthetic nucleotide sequence that is designed to minimize the interaction of expression elements in neighboring transgenic cassettes on each other's expression. The Intergenic Sequence Regions disclosed herein were computationally-designed and assayed for the ability to reduce the interaction of a first transgene expression cassette on a second transgene expression cassette in a vector stack used to transform plant cells, thus preserving the expression profile of each transgene expression cassette as that when observed individually in a transgenic plant.

A "synthetic nucleotide sequence" or "artificial nucleotide sequence" is a nucleotide sequence that is not known to occur in nature or that is not naturally occurring. The Intergenic Sequence Region elements of the present invention comprise synthetic nucleotide sequences. Preferably, synthetic nucleotide sequences share little or no extended homology to natural sequences. Extended homology in this context generally refers to 100% sequence identity extending beyond about 25 nucleotides of contiguous sequence.

In Example 2, control corn plants were transformed using two vector stacks comprised of two transgene expression cassettes in a divergent orientation. One control vector stack comprised a first transgene expression cassette comprising a rice actin one promoter (Control without Enhancer, see FIG. 1a) driving expression of an antibiotic resistance gene and a second transgene expression cassette that comprised a seed-preferred promoter driving GUS expression. Corn plants transformed with this vector stack demonstrated seed-preferred expression of GUS. The other control vector stack (Control with Enhancer) comprised a first transgene expression cassette comprising a strong enhancer derived from CaMV 35S operably linked to the rice actin one promoter driving expression of an antibiotic resistance gene and a second transgene expression cassette that comprised a seed-preferred promoter driving GUS expression. Corn plants transformed with the Control with Enhancer demonstrated high levels of GUS expression in roots, leaves, anther, silk, and seed. Thus, in the Control with Enhancer, the first transgene expression cassette enhancer modified the expression pattern of the second expression transgene cassette's expression profile, changing the expression of the second expression transgene cassette from seed-preferred to constitutive.

Certain computationally-designed ISRs were inserted between the first and second transgene cassettes of the Control with Enhancer, as demonstrated in FIG. 1c. The percent leakiness in the interaction of the first transgene expression cassette's expression pattern on the second transgene expression cassette's expression pattern was 16%. 8%, and 6%, respectively, when the ISRs ISR4_Stop (SEQ ID NO:1), ISR89 (SEQ ID NO:2), and ISR97 (SEQ ID NO:5) were inserted between the first and second transgene expression cassettes. Thus, these ISRs reduced the interaction of the first transgene expression cassette with the second transgene expression cassette by 84%, 92%, and 94%, respectively.

In Example 3, a similar experimental design was used to test the effectiveness of certain ISRs in soybeans. Insertion of ISR2 (SEQ ID NO:3). ISR4 (SEQ ID NO:4), ISR69 (SEQ ID NO:6) between the first transgene expression cassette and second transgene expression cassette of the Control with Enhancer resulted in a reduction of the effect of the first transgene expression cassette's expression pattern on the second transgene expression cassette's with only 3%, 4%, and 5% leakiness, respectively. This resulted in a reduction in interaction of the expression elements in the first transgene expression cassette on the second transgene expression cassette's expression pattern by 97%, 96%, and 95%, respectively.

As demonstrated in the Examples, not all computationally-designed Intergenic Sequence Regions were as efficacious in reducing interaction. Further, even ISRs which resulted in reduction of interaction did so to varying degrees. For example, ISR88 (SEQ ID NO:7) and ISR86 (SEQ ID NO:8) only reduced interaction by 39% and 68%, respectively in transgenic corn plants with a leakiness of 61% and 32%, respectively. This reduction in the interaction was much less when compared to 84% for ISR4_Stop, 92% for ISR89, and 94% for ISR97. Likewise, in transgenic soybeans ISR_X (SEQ ID NO:9) only reduced the interaction by 76% (percent leakiness, 24%) in comparison to 97% for ISR2, 96% for ISR4, and 95% for ISR69. Thus, each computationally designed ISR is unique, and different ISRs can be used in conjunction with different expression cassettes to reach the desired expression profiles for one or more genes of interest.

DNA Molecules

As used herein, the term "DNA" or "DNA molecule" refers to a double-stranded DNA molecule of genomic or synthetic origin. i.e., a polymer of deoxyribonucleotide bases or a DNA molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998). Appendix 2, Tables 1 and 3.

As used herein, a "heterologous molecule" is a molecule comprising a combination of DNA molecules that would not naturally occur together without human intervention. For instance, a heterologous molecule may be a DNA molecule that is comprised of at least two DNA molecules heterologous with respect to each other, a DNA molecule that comprises a DNA sequence that deviates from DNA sequences that exist in nature, a DNA molecule that comprises a synthetic DNA sequence or a DNA molecule that has been incorporated into a host cell's DNA by genetic transformation or gene editing.

Reference in this application to an "isolated DNA molecule" or an equivalent term or phrase is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As used herein, the term "sequence identity" refers to the extent to which two optimally aligned polynucleotide sequences or two optimally aligned polypeptide sequences are identical. An optimal sequence alignment is created by manually aligning two sequences, e.g., a reference sequence and another sequence, to maximize the number of nucleotide matches in the sequence alignment with appropriate internal nucleotide insertions, deletions, or gaps. As used herein, the term "reference sequence" refers to a DNA sequence provided as SEQ ID NOs:1-6.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a sequence that, when optimally aligned to a reference sequence, provided herein as SEQ ID NOs:1-6, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence. In certain embodiments, a sequence having a given percent identity to any of SEQ ID NOs: 1-6 maintains the general functionality of any of SEQ ID NOs: 1-6, i.e., exhibits the same or similar capacity to reduce the influence of a first transgene expression cassette on the expression of a second transgene cassette in a transgenic plant. In certain embodiments, a sequence having a given percent identity to any of SEQ ID NOs: 1-6 has the activity of any of SEQ ID NOs: 1-6 with respect to reducing the influence of a first transgene expression cassette on the expression of a second transgene cassette in a transgenic plant.

Regulatory Elements

Regulatory elements such as promoters, leaders (also known as 5' UTRs), enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are useful for modifying plant phenotypes through genetic engineering.

Regulatory elements may be characterized by their gene expression pattern. e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), a small interfering RNA (siRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may be initially isolated from the 5' untranslated region (5' UTR) of a genomic copy of a gene. Alternately, promoters may be synthetically produced or manipulated DNA molecules. Promoters may also be chimeric. Chimeric promoters are produced through the fusion of two or more heterologous DNA molecules. Promoters useful in demonstrating the present invention include promoter elements provided as SEQ ID NOs: 11, 16, 21, and 25.

As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Leaders useful in demonstrating the present invention include SEQ ID NOs: 12, 17, 22, and 26.

As used herein, the term "intron" refers to a DNA molecule that may be isolated or identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Introns useful in demonstrating the present invention are presented as SEQ ID NOs:13 and 18.

As used herein, the terms "3' transcription termination molecule," "3' untranslated region" or "3' UTR" refer to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation.

As used herein, the term "enhancer" or "enhancer element" refers to a cis-acting regulatory element, a.k.a. cis-element, which confers an aspect of the overall expression pattern, but is usually insufficient alone to drive transcription, of an operably linked transcribable DNA molecule. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

As used herein, the term "variant" refers to a second DNA molecule that is in composition similar, but not identical to, a first DNA molecule. For example, a variant of one of the ISRs disclosed herein would have a slightly different sequence composition but would maintain the capacity to reduce the influence of a first transgene expression cassette on the expression of a second transgene cassette in a transgenic plant in the same manner as the ISR from which it was derived. A variant may be a shorter or truncated version of the first DNA molecule or an altered version of the sequence of the first DNA molecule, such as one with different restriction enzyme sites and/or internal deletions, substitutions, or insertions. A "variant" can also encompass an ISR having a nucleotide sequence comprising a substitution, deletion, or insertion of one or more nucleotides of a reference sequence, wherein the derivative Intergenic Sequence Region element has more or less or equivalent capacity to reduce the influence of a first transgene expression cassette on the expression of a second transgene cassette in a transgenic plant. In the present invention, a polynucleotide sequence provided as SEQ ID NOs:1-6 may be used to create variants that are similar in composition, but not identical to, the DNA sequence of the original ISR, while still maintaining the general functionality, i.e., the same or similar capacity to reduce the influence of a first transgene expression cassette on the expression of a second transgene cassette in a transgenic plant. In certain embodiments, a variant of any of SEQ ID NOs: 1-6 has the activity of any of SEQ ID NOs: 1-6 with respect to reducing the influence of a first transgene expression cassette on the expression of a second transgene cassette in a transgenic plant. Production of such variants of the invention is well within the ordinary skill of the art in light of the disclosure and is encompassed within the scope of the invention.

In certain examples, a variant of an ISR may be a fragment of any of SEQ ID NOs: 1-6. Fragments of SEQ ID NOs: 1-6 may comprise at least about 50 contiguous nucleotides, at least about 100 contiguous nucleotides, at least about 150 contiguous nucleotides, at least about 200 contiguous nucleotides, at least about 250 contiguous nucleotides, at least about 300 contiguous nucleotides, at least about 350 contiguous nucleotides, at least about 400 contiguous nucleotides, at least about 450 contiguous nucleotides, at least about 500 contiguous nucleotides, at least about 550 contiguous nucleotides, at least about 600 contiguous nucleotides, at least about 650 contiguous nucleotides, at least about 700 contiguous nucleotides, at least about 750 contiguous nucleotides, at least about 800 contiguous nucleotides, at least about 850 contiguous nucleotides, at least about 900 contiguous nucleotides, at least about 950 contiguous nucleotides, at least about 1000 contiguous nucleotides, at least about 1100 contiguous nucleotides, at least about 1200 contiguous nucleotides, at least about 1300 contiguous nucleotides, at least about 1400 contiguous nucleotides, at least about 1500 contiguous nucleotides, at least about 1600 contiguous nucleotides, at least about 1700 contiguous nucleotides, at least about 1800 contiguous nucleotides, at least about 1900 contiguous nucleotides, at least about 2000 contiguous nucleotides, at least about 2100 contiguous nucleotides, at least about 2200 contiguous nucleotides, at least about 2300 contiguous nucleotides, at least about 2400 contiguous nucleotides, at least about 2500 contiguous nucleotides, at least about 2600 contiguous nucleotides, at least about 2700 contiguous nucleotides, at least about 2800 contiguous nucleotides, at least about 2900 contiguous nucleotides, at least about 3000 contiguous nucleotides, or more of any of SEQ ID NOs: 1-6. In certain embodiments, a fragment of any of SEQ ID NOs: 1-6 has the activity of any of SEQ ID NOs: 1-6 with respect to reducing the influence of a first transgene expression cassette on the expression of a second transgene cassette in a transgenic plant.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A "vector stack" is a vector comprised of two or more cassettes stacked together for transformation. Two or more transgene expression cassettes in a vector stack are separated by fragments of DNA sequence which can be as few as approximately 10 nucleotides to approximately several hundred nucleotides, or several thousand nucleotides, or more, depending upon the method of cloning or synthesis that was used to construct the vector stack. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Transcribable DNA Molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell. In certain embodiments, a transgene comprises a gene of agronomic interest, such as a gene capable of providing herbicide resistance in plants, or a gene capable of providing plant pest resistance in plants.

A regulatory element, such as a promoter, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, a DNA molecule that comprises a synthetic DNA sequence or a DNA molecule that has been incorporated into a host cell's DNA by genetic transformation or gene editing.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance. Examples of selectable marker transgenes is provided as SEQ ID NOs:18 and 26.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct or a vector stack, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also include progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), and gene editing (e.g., CRISPR-Cas systems), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, CA, 50-98 (1960); Simmonds, *Principles of Crop Improvement*, Longman, Inc., NY, 369-399 (1979); Sneep and Hendriksen, *Plant breeding Perspectives*, Wageningen (ed). Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique,* (Vol. 1) and *Crop Species Soybean* (Vol. 2). Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems. Foster City, CA) reagents and methods as described by the manufacturer and PCR cycle times determined using the TaqMan® Testing Matrix. Alternatively, the Invader® (Third Wave Technologies, Madison, WI) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NOs:1-6. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following Examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Design, Synthesis, and Cloning of the Intergenic Sequence Region Elements

Synthetic Intergenic Sequence Region elements ("ISRs") were computationally-designed through algorithmic methods. Each ISR was designed to not contain any potential Open Reading Frames (ORF) that could inadvertently lead to the production of unwanted proteins after insertion into the plant genome. In addition, many of the ISRs were designed to contain stop codons at the 5' and 3' ends of the ISR, positioned in a manner to provide stop codons in all six reading frames.

Once designed, the ISRs were chemically synthesized and cloned between transgene expression cassettes in a heterologous vector stack. Well over 100 synthetic Intergenic Sequence Region elements were designed and assayed in stably transformed corn and soybean plants to identify those synthetic ISRs that reduced the interaction of a first transgene cassette with a second transgene cassette.

Certain designed and tested ISRs are presented in Table 1. ISR4_Stop is a variant of ISR4, wherein stop codons were appended to the 3' and 5' ends of ISR4.

TABLE 1

Synthetic Intergenic Sequence Region Elements.

| Description | SEQ ID NO: | Size (bp) | ORFs Present | Stop codons in all 6 frames |
|---|---|---|---|---|
| ISR4_Stop | 1 | 1219 | No | Yes |
| ISR89 | 2 | 1024 | No | Yes |
| ISR2 | 3 | 1195 | No | No |
| ISR4 | 4 | 1195 | No | No |
| ISR97 | 5 | 3024 | No | Yes |
| ISR69 | 6 | 1035 | No | Yes |
| ISR88 | 7 | 1024 | No | Yes |
| ISR86 | 8 | 1024 | No | Yes |
| ISK_X | 9 | 1219 | No | Yes |

The synthetic Intergenic Sequence Region elements presented as SEQ ID NOs:1-6 demonstrated the ability to reduce the interaction of a first transgene cassette on a second transgene cassette in a vector stack in stably transformed corn and soybean plants as presented in Examples 2 and 3.

Example 2

Reduction of Transgene Expression Cassette Interaction by ISR4_Stop, ISR89, and ISR97 in Stably Transformed Corn Plants This Example demonstrates the ability of the ISRs ISR4_Stop, ISR89, and ISR97 to reduce transgene expression cassette interaction when inserted between a rst transgene expression cassette and a second transgene expression cassette of a vector stack used to stably transform corn plants.

Corn plants were transformed with binary plant transformation vector stacks comprising two transgene expression cassettes in divergent orientation with an ISR between the two transgene expression cassettes to assess the ability of the ISR to reduce transgene expression cassette interaction. Two control vector stacks were also transformed into corn plants and tested.

One control vector stack (FIG. 1a, Control without Enhancer) comprised a first transgene expression cassette which comprised a promoter. P-Os.Act1:67 (SEQ ID NO:11), operably linked 5' to a leader, L-Ta.Lhcb1:1 (SEQ ID NO:12), operably linked 5' to an intron, I-Os.Act1-1:1:19 (SEQ ID NO:13), operably linked 5' to a coding sequence for neomycin phosphotransferase, CR-Ec.nptII-Tn5-1:1:3 (SEQ ID NO:14), operably linked 5' to a 3' UTR, T-Ta.Hsp17-1:1:1 (SEQ ID NO:15). The second transgene expression cassette cloned in a divergent orientation relative to the first transgene expression cassette comprised a seed-specific promoter. P-Zm.39486-1:1:1 (SEQ ID NO:16), operably linked 5' to a leader, L-Zm.39486-1:1:1 (SEQ ID NO:17), operably linked 5' to an intron, I-Zm.DnaK:1 (SEQ ID NO:18), operably linked 5' to a coding sequence encoding GUS-1, GOI-Ec.uidA+St.LS1.nno:1 (SEQ ID NO:19), operably linked 5' to a 3' UTR, T-Os.Mth-1:1:1 (SEQ ID NO:20). The Control without Enhancer vector stack also comprised an additional transgene expression cassette which was used for selection of the transformed cells using glyphosate selection.

The other control vector stack (FIG. 1b, Control with Enhancer) comprised a first transgene expression cassette which comprised a strong enhancer, E-CaMV.35S.2xA1-B3-1:1:1 (SEQ ID NO:10) comprising tandem repeats of specific enhancer regions derived from the Cauliflower mosaic virus 35S promoter, operably linked 5' to a promoter, P-Os.Act1:67 (SEQ ID NO:11), operably linked 5' to a leader, L-Ta.Lhcb1:1 (SEQ ID NO:12), operably linked 5' to an intron, I-Os.Act1-1:1:19 (SEQ ID NO:13), operably linked 5' to a coding sequence for neomycin phosphotransferase, CR-Ec.nptII-Tn5-1:1:3 (SEQ ID NO:14), operably linked 5' to a 3' UTR, T-Ta.Hsp17-1:1:1 (SEQ ID NO:15). The second transgene expression cassette cloned in a divergent orientation relative to the first transgene expression cassette comprised a seed-specific promoter and was the same transgene expression cassette as described above. The Control with Enhancer vector stack also comprised an additional transgene expression cassette which was used for selection of the transformed cells using glyphosate selection.

To assay the effectiveness of an ISR in reducing the interaction between a first and second transgene expression cassette, the ISRs ISR4_Stop (SEQ ID NO:1), ISR89 (SEQ ID NO:2), ISR97 (SEQ ID NO:5), ISR88 (SEQ ID NO:7), and ISR86 (SEQ ID NO:8) were cloned between the first and second transgene expression cassettes of the Control with Enhancer vector stack, as depicted in FIG. 1c. Variety LH244 corn plant cells were transformed using an Agrobacterium-mediated transformation method similar to those known in the art with the two control vector stacks and the five vector stacks comprising the ISRs. The transformed plant cells were induced to form whole plants.

Qualitative and quantitative GUS analysis was used to evaluate expression element activity in selected plant organs and tissues in the transformed plants. For qualitative analysis of GUS expression by histochemical staining, wholemount or sectioned tissues were incubated with GUS staining solution containing 1 mg/mL of X-Gluc (5-bromo-4-chloro-3-indolyl-b-glucuronide) for 5 h at 37° C. and de-stained with 35% EtOH and 50% acetic acid. Expression of GUS was qualitatively determined by visual inspection of 5 selected plant organs or tissues for blue coloration under a dissecting or compound microscope. For quantitative analysis of GUS expression by enzymatic assays, total protein was extracted from selected tissues of transformed corn plants. One to two micrograms of total protein was incubated with the fluorogenic substrate, 4-methyleumbelliferyl-β-D-glucuronide (MUG) at 1 mM concentration in a total reaction volume of 50 microliters. After 1 h incubation at 37° C. the reaction was stopped by adding 350 microliters of 200 mM sodium bicarbonate solution. The reaction product, 4-methylumbelliferone (4-MU), is maximally fluorescent at high pH, where the hydroxyl group is ionized. Addition of the basic sodium carbonate solution simultaneously stops the assay and adjusts the pH for quantifying the fluorescent product 4-MU. The amount of 4-MU formed was estimated by measuring its fluorescence using a FLUOstar Omega Microplate Reader (BMG LABTECH) (excitation at 355 nm, emission at 460 nm). GUS activity values are provided in nmoles of 4-MU/hour/mg total protein.

The following tissues were sampled for GUS expression in the $R_0$ generation: V3 stage Leaf and Root; V7 stage Leaf and Root; VT stage Leaf, Root, and Anther and Silk; and R3 stage Seed Embryo and Seed Endosperm 21 days after pollination (DAP). Table 2 shows the mean GUS expression in the vegetative, reproductive, and seed tissues, wherein "bdl" indicates GUS expression was below the levels of detection. Table 3 shows the average GUS expression in the vegetative and reproductive tissues. The Control with Enhancer is considered to represent the full interaction of the first transgene expression cassette enhancer with the seed-specific promoter of the second transgene expression cassette. Therefore, the average vegetative and reproductive tissue expression from the GUS cassette which was driven by the P-Zm.39486-1:1:1, seed-specific promoter affected by the strong constitutive enhancer of the first transgene expression cassette represents a leakiness of 100 percent. The percent leakiness of the vector stacks comprising an ISR were determined by dividing the average GUS expression in the vegetative and reproductive tissues of plants transformed with constructs comprising an ISR by the average GUS expression in the vegetative and reproductive tissues of the Control with Enhancer, and multiplying the result by one-hundred.

TABLE 3

Average Vegetative and Reproduction GUS Expression and Mean Percent Leakiness of ISRs compared to controls.

| Control/ISR | SEQ ID NO: | Average Vegetative and Reproductive Expression | % Leakiness |
|---|---|---|---|
| Control without Enhancer | | 12 | 1% |
| Control with Enhancer | | 1070 | 100% |
| ISR4_Stop | 1 | 172 | 16% |
| ISR89 | 2 | 87 | 8% |
| ISR97 | 5 | 55 | 6% |
| ISR88 | 7 | 652 | 61% |
| ISR86 | 8 | 346 | 32% |

As can be seen in Table 2, the Control with Enhancer demonstrated high GUS expression in all tissues of stably transformed corn plants when compared to the Control without Enhancer. This demonstrates that the strong enhancer in the first transgene expression cassette modified the seed-specific expression pattern of the second transgene expression cassette to a more constitutive expression pattern.

As shown in Table 2, the interaction of the strong enhancer in the first transgene expression cassette on the second transgene expression cassette was reduced when the ISRs ISR4_Stop, ISR89, and ISR97 were inserted between the cassettes. The average GUS expression of the vegetative and reproductive tissues in the vector stacks with ISR4_Stop, ISR89 and ISR97 were much less than that of the Control with Enhancer vector. The percent leakiness of ISR4_Stop, ISR89, and ISR97 was 16%, 8%, and 6%, respectively, thus providing a reduction in the interaction between the two transgene expression cassettes by 84%, 92%, and 94%, respectively. In comparison, ISR88 and ISR86 were much leakier (61% and 32%, respectively), and only reduced the interaction between the two transgene expression cassettes by 39% and 68%, respectively.

ISR4_Stop (SEQ ID NO:1), ISR89 (SEQ ID NO:2), and ISR97 (SEQ ID NO:5) demonstrated the ability to reduce the interaction of a first transgene expression cassette with a second transgene expression cassette in a vector stack in stably transformed corn plants.

TABLE 2

Mean GUS expression in vegetative, reproductive, and seed tissues of LH244 stable transformed corn plants.

| Control/ISR | SEQ ID NO: | V3-root | V3-leaf | V7-root | V7-leaf | VT-root | VT-leaf | VT-Anther | VT-silk | 21-DAP-Em | 21-DAP-Endo |
|---|---|---|---|---|---|---|---|---|---|---|---|
| Control without Enhancer | | 23 | bdl | 46 | 11 | bdl | bdl | 19 | bdl | 13 | 215 |
| Control with Enhancer | | 1469 | 1310 | 1847 | 1698 | 367 | 946 | 323 | 603 | 68 | 2651 |
| ISR4_Stop | 1 | 409 | 71 | 255 | 84 | 169 | 60 | 296 | 31 | 197 | 1169 |
| ISR89 | 2 | 140 | 75 | 146 | 39 | 110 | 27 | 113 | 41 | 24 | 560 |
| ISR97 | 5 | 35 | 39 | 22 | 78 | 38 | 41 | 146 | 41 | 27 | 269 |
| ISR88 | 7 | 789 | 169 | 142 | 217 | 1671 | 456 | 1349 | 426 | 62 | 3033 |
| 1SR86 | 8 | 370 | 355 | 144 | 90 | 712 | 380 | 628 | 85 | 40 | 1645 |

Example 3

Reduction of Transgene Expression Cassette Interaction by ISR2 and ISR4 in Stably Transformed Soybean Plants This Example demonstrates the ability of the Intergenic Sequence Region elements. ISR2 and ISR4 to reduce transgene expression cassette interaction when inserted between a first transgene expression cassette and a second transgene expression cassette of a vector stack used to stably transform soybean plants.

Soybean plants were transformed with binary plant transformation vector stacks comprising two transgene expression cassettes in divergent orientation with an ISR between the two transgene expression cassettes to assess the ability of the ISR to reduce transgene expression cassette interaction. Two control vector stacks were also transformed into soy plants and tested.

One control vector stack (FIG. 2a, Control without Enhancer) comprised a single transgene expression cassette comprised of a seed-specific promoter. P-Gm.Sphas1:14 (SEQ ID NO:25), operably linked 5' to a leader, L-Gm.Sphas1-1:1:1 (SEQ ID NO:26), operably linked 5' to a coding sequence encoding GUS-2. GOI-GUS:1:2 (SEQ ID NO:27), operably linked 5' to a 3' UTR, T-Mt.AC145767v28:3 (SEQ ID NO:28). The Control without Enhancer vector stack also comprised an additional transgene expression cassette which was used for selection of the transformed cells using antibiotic selection.

Figure 2B:
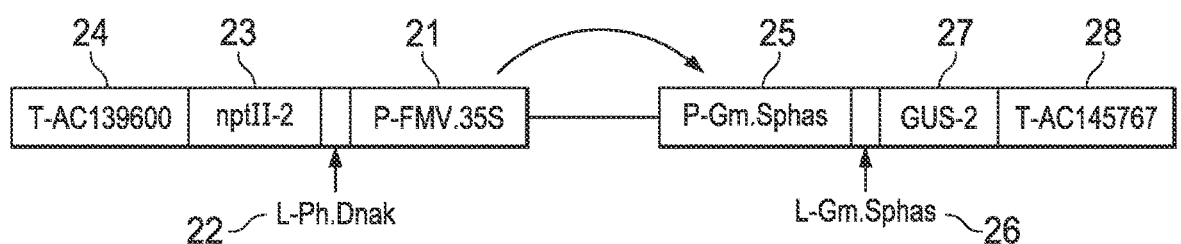

The other control vector stack, (FIG. 2b, Control with Enhancer) comprised two transgene expression cassettes in divergent orientation. The first transgene cassette comprised a strong promoter derived from the Figwort mosaic virus 35S promoter with a rearranged and duplicated enhancer. P-FMV.35S-enh-1:1:2 (SEQ ID NO:21), operably linked 5' to a leader, L-Ph.DnaK-1:1:3 (SEQ ID NO:22), operably linked 5' to a coding sequence for neomycin phosphotransferase. CR-Ec.nptII-Tn5-1:1:2 (SEQ ID NO:23), operably linked 5' to a 3' UTR, T-Mt.AC139600v16:1 (SEQ ID NO:24). The second transgene expression cassette was the same as the seed-specific transgene expression cassette described above. The Control with Enhancer vector stack also comprised an additional transgene expression cassette which was used for selection of the transformed cells using antibiotic selection.

Figure 2C:
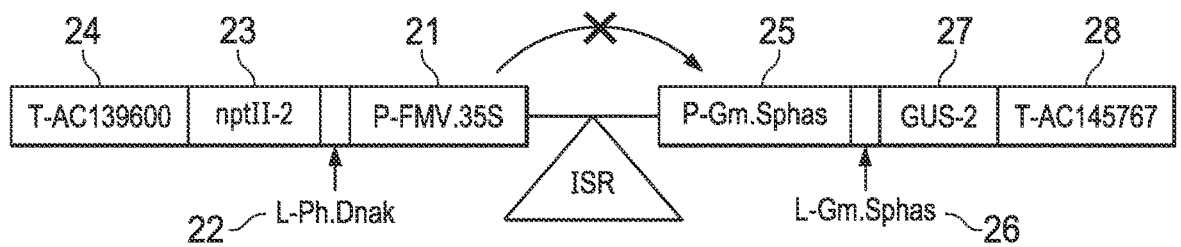

To assay the effectiveness of an ISR in reducing the interaction between a first and second transgene expression cassette, the ISRs ISR2 (SEQ ID NO:3). ISR4 (SEQ ID NO:2). ISR69 (SEQ ID NO:6), and ISR_X (SEQ ID NO:8) were cloned between the first and second transgene expression cassettes of the Control with Enhancer vector stack as depicted in FIG. 2c. Variety A3555 soybean plant cells were transformed using an Agrobacterium-mediated transformation method similar to those known in the art with the Control without Enhancer, the Control with Enhancer, and the three vector stacks comprising the ISRs. The transformed plant cells were induced to form whole plants.

Qualitative and quantitative GUS analysis was performed as previously described in Example 2. The following tissues were sampled for GUS expression in the $R_0$ generation: Vn5 Root, Vn5 Sink Leaf, Vn5 Source Leaf, R1 Source Leaf, R1 Petiole, R1 Flower, R3 Immature seed, R3 Pod, R5 Cotyledon, Yellow Pod (YP) Embryo, and Yellow Pod (YP) Cotyledon.

The Control with Enhancer is considered to represent the full interaction of the first transgene expression cassette enhancer with the seed-specific promoter of the second transgene expression cassette. Therefore, the average vegetative and reproductive tissue expression from the GUS cassette which was driven by the P-Gm.Sphas1:14, seed-specific promoter, affected by the strong constitutive enhancer of the first transgene expression cassette, represents a leakiness of 100 percent. The percent leakiness of the constructs comprising an ISR were determined by dividing the average GUS expression in the Vn5, R1, and R3 tissues of plants transformed with constructs comprising an ISR by the average GUS expression of the Vn5, R1, and R3 tissues of the Control with Enhancer, and multiplying the result by one-hundred.

The Mean GUS expression of the Vn5, R1, and R3 tissues is presented in Table 4, wherein "nd" indicates not determined. The Mean GUS expression of R5 and Yellow Pod tissues, the average Vn5, R1, and R3 tissue expression, and the percent leakiness is presented in Table 5.

TABLE 4

Mean GUS expression of Vn5, R1, and R3 tissues in stably transformed A3555 soybean plants.

| Control/ISR | SEQ ID NO: | Vn5 Root | Vn5 Sink Leaf | Vn5 Source Leaf | R1 Source Leaf | R1 Petiole | R1 Flower | R3 Immature Seed | R3 Pod |
|---|---|---|---|---|---|---|---|---|---|
| Control No Enhancer | | 10 | 3 | 4 | 0 | 0 | 0 | 11 | 8 |
| Control With Enhancer | | 3072 | 2524 | 1939 | 2722 | 6369 | 2434 | 520 | 6236 |
| ISR2 | 3 | 113 | 69 | 107 | 39 | 155 | 56 | 45 | 112 |
| ISR4 | 4 | 207 | 33 | 86 | 28 | 349 | 84 | 31 | 97 |
| ISR69 | 6 | 108 | 74 | 62 | 76 | 488 | 311 | 113 | 64 |
| ISR_X | 9 | 391 | 107 | 121 | 103 | 974 | 179 | nd | 3654 |

TABLE 5

Mean GUS expression of R5 and Yellow Pod tissues, the average Vn5, R1, and R3 tissue expression, and the percent leakiness in stably transformed A3555 soybean plants.

| Control/ISR | SEQ ID NO: | R5 Cotyledon | Yellow Pod Embryo | Yellow Pod Cotyledon | Average Vn5, R1, and R3 | % leakiness |
|---|---|---|---|---|---|---|
| Control No Enhancer | | 47 | 1445 | 4264 | 5 | 0% |
| Control With Enhancer | | 2673 | 6746 | 6294 | 3227 | 100% |
| ISR2 | 3 | 3330 | 6308 | 6703 | 87 | 3% |

TABLE 5-continued

Mean GUS expression of R5 and Yellow Pod tissues, the average Vn5, R1, and R3 tissue expression, and the percent leakiness in stably transformed A3555 soybean plants.

| Control/ISR | SEQ ID NO: | R5 Cotyledon | Yellow Pod Embryo | Yellow Pod Cotyledon | Average Vn5, R1, and R3 | % leakiness |
|---|---|---|---|---|---|---|
| ISR4 | 4 | 10066 | 3881 | 6267 | 114 | 4% |
| ISR69 | 6 | 3223 | 4114 | 5432 | 162 | 5% |
| ISR_X | 9 | 5049 | 11495 | 11767 | 790 | 24% |

As can be seen in Table 4, very little GUS expression is observed in the Vn5, R1, and R3 tissues in plants transformed with the Control without Enhancer. Plants transformed with the Control with Enhancer demonstrate a constitutive expression pattern, with high GUS expression observed in the Vn5, R1, and R3 tissues. Likewise, as seen in Table 5, plants transformed with the Control without Enhancer only demonstrate high GUS expression in the Yellow Pod Embryo and Cotyledon, consistent with the known seed-specific expression pattern of P-Gm.Sphas1:14. Very little expression is observed in the R5 Cotyledon wherein expression is seen to increase slightly relative to R3 Immature Seed. Plants transformed with the Control with Enhancer show high levels of expression in the R5 cotyledon and an increase in the Yellow Pod Embryo and Cotyledon relative to Plants transformed with the Control without Enhancer. Thus, the strong enhancer comprised in the P-FMV.35S-enh-1:1:2 promoter of the first transgene expression cassette of the Control with Enhancer interacted with, and changed the seed-specific expression of P-Gm.Sphas1:14 of the second transgene expression cassette, to a constitutive expression pattern.

As demonstrated in Table 5, the Intergenic Sequence Regions ISR2. ISR4, and ISR69 were able to reduce the interaction of the first transgene expression cassette on the second transgene expression cassette of the Control with Enhancer configuration by 97%. 96%, and 95%, respectively (were only 3%. 4%, and 5% leaky). The ISR_X was not as effective in reducing the interaction of the first transgene expression cassette on the second transgene expression cassette of the Control with Enhancer configuration and demonstrated a leakiness of 24%. ISR_X only reduced the interaction by 76% in comparison to 97%, 96%, 95% for ISR2, ISR4, and ISR69.

ISR2 (SEQ ID NO:3), ISR4 (SEQ ID NO:4), and ISR69 (SEQ ID NO:6) demonstrated the ability to reduce the interaction of a first transgene expression cassette with a second transgene expression cassette in stably transformed soybean plants.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a polynucleotide comprising a DNA sequence selected from the group consisting of:
   a) a sequence with at least 95 percent sequence identity to SEQ ID NO:2, wherein said polynucleotide comprising said DNA sequence reduces the influence of a first transgene expression cassette on the expression of a second transgenic expression cassette in a transgenic plant; and
   b) a sequence comprising SEQ ID NO:2.

2. The recombinant DNA molecule of claim 1, wherein the DNA sequence is inserted between a first expression cassette and a second expression cassette in a vector stack.

3. The recombinant DNA molecule of claim 1, wherein the DNA sequence has at least 97 percent sequence identity to the DNA sequence of SEQ ID NO:2.

4. The recombinant DNA molecule of claim 1, wherein the DNA sequence has at least 99 percent sequence identity to the DNA sequence of SEQ ID NO:2.

5. The recombinant DNA molecule of claim 1, wherein the DNA sequence comprises SEQ ID NO:2.

6. A transgenic plant cell comprising the recombinant DNA molecule of claim 1.

7. The transgenic plant cell of claim 6, wherein said transgenic plant cell is a monocotyledonous plant cell.

8. The transgenic plant cell of claim 6, wherein said transgenic plant cell is a dicotyledonous plant cell.

9. A transgenic plant, or part thereof, comprising the recombinant DNA molecule of claim 1.

10. A progeny plant of the transgenic plant of claim 9, or a part thereof, wherein the progeny plant or part thereof comprises the recombinant DNA molecule.

11. A transgenic seed, wherein the seed comprises the recombinant molecule of claim 1.

12. A method of producing a commodity product comprising obtaining the transgenic plant or part thereof according to claim 9 and producing the commodity product therefrom.

13. The method of claim 12, wherein the commodity product is selected from the group consisting of seeds, processed seeds, protein concentrate, protein isolate, starch, grains, plant parts, seed oil, biomass, flour, and meal.

14. A method for reducing the interaction of a first transgene expression cassette with a second transgene expression cassette within a transgenic plant transformed with a vector stack, said method comprising transforming a plant cell with a vector stack comprising a heterologous T-DNA comprising:
   a) a first transgene expression cassette;
   b) a second transgene cassette;
   c) the recombinant DNA molecule of claim 1, wherein the DNA molecule is inserted between the first transgene expression cassette and the second transgene expression cassette; and
   d) regenerating a transgenic plant from the transformed plant cell.

15. The method of claim 14, wherein the DNA molecule of SEQ ID NO:2 is inserted between the first transgene expression cassette and the second transgene expression cassette within the vector stack.

* * * * *

SEQUENCE LISTING

```
<160> NUMBER OF SEQ ID NOS: 28

<210> SEQ ID NO 1
<211> LENGTH: 1219
<212> TYPE: DNA
<213> ORGANISM: Artificial
<220> FEATURE:
<223> OTHER INFORMATION: DNA sequence of an Intergenic Sequence Region
      or ISR, ISR4_Stop.

<400> SEQUENCE: 1
ttagttagtt agcgtcagcc cctccaaggt ggatcaagac tgcaccggca agcagtgtag        60
tctctctttc tagatttggc aaagtcactt gtcggagcgg tgtgatcgca cgctttagcg       120
cggcgagagc gtcctcgcga gttatcccca ggctcgccaa ggcccgtgtt gcgcgtatca       180
agaatcttag agttcgactg ctgttcacag aggagctaag gagattggac cgtgccgctg       240
aacagccaga tccaccgggg gctccggacc taagctgcta aagatttcgc aagcggaatc       300
cgccaaatct atacagatcc gaaccagaca ggcgactacg ccgttgatca ggggtgaagt       360
tacttactat cggatctatc gtcgcaagga gagacggttt ctggaaacgg cccactcacg       420
tctgctggtc tacacgggtc ttaaatatcg gatagaatcg cttatccgcg gcttctagca       480
agcagagaga acaacgtctt ctttcgcgcc cgtgcgactt caataaattg cgagcaattg       540
```

```
cccgtagccc aaaaataaaa atcgatcagg ctaccagaac gatcaggcag gtacttatat    600
tgtaatcaag ggaaatttta acgagttccg acaaggtgga agccagattg tatcacttaa    660
ggcttctgct tccaactact taccctcacc accacttacg cttcacctca agaagtaact    720
tcgtggttct gtacgccgga gagctgctcg gtaattaacg actaggacca gcggagcctt    780
agctttagag atcacttgaa ctacaccact ttcgactggg aagtagcagg cagccttctc    840
tccgcgggta acgtcgaatc tgctgatcgg cgtgcagctg gccttaaatc tgaactcgtc    900 cgccttttc tgttgaccaa gagtggaaaa agtggcccgc tcttttaaa tcagcgtgac     960 ttcgcgaaac tccttcgttc tgtgaagggt gtggcttttg cttagaccta acgtcgccg   1020 tggtacgctt cggaacacct gcggggtcga ttcgatctcc aggtcgagtt cagctcagta  1080
aaggtttata tcaccgtaaa gtctgagccg tccgactgag cacaaattaa cacagtatta  1140
cgacagggag tattacaata gatttgcagc gcgggaccct ctcagatcaa cggttgtaca  1200
cgataattta gttagttag                                               1219

<210> SEQ ID NO 2
<211> LENGTH: 1024
<212> TYPE: DNA
<213> ORGANISM: Artificial
<220> FEATURE:
<223> OTHER INFORMATION: DNA sequence of an Intergenic Sequence Region
      or ISR, ISR89.

<400> SEQUENCE: 2
ctagctaact aagcttcctc ccaggttttc gggactcgcc agacctaaat tattcccgtt     60
tgttgccgct accgggcctc ggtggggccc tccctggcac tccgggctga gcgcacgcgt    120
aattacgccg acctagcgat tggtgaaccc gacaagaagg tgcgggccta gttggcgggc    180
ttggggccta cccgcgtggg ctgaacagaa ggaaccctca agtgaaagag tttgaaactg    240
ggcgtcacct cggactaatt actcgcgtgg cacgtgctcc gggtcggccc tgaggctgta    300
ggcgcaaagc gaaagtccag gataggggag aggacggcca acccgcctcg gtatcctgga    360
ttcctaacct ctgaccggat cagcaatatc gctccacact aaccgccccc ttttccgact    420
ccgggtgctc ttcgcggagt tggctagaga caagtgagca cggatcagac gcgagagagg    480
caatcgttta tttgtaagcg cctactgccc caaccgatcg cggtgtgcag agaggattgt    540
gctatactga agcgggtgtg tcactaaggg ttgcggtggg aagcccgggc agtgactaag    600
cctgatccga gccccaggc actactccga cctttagca cgttgtgacg gtctgccaag     660
ggttctcacg ttaatttagc gatcgggta acaagggcca gaacggtccc ccctgtatca    720
ccgctctgca gtggagtttt ccccagcgtc ctcaaatcgt gggactcggc aggcggtcac    780
tgcccagccc gtgtataagg tagggctccc gtactgtacg aaataatatc cctgtaactc    840
tgttcgcccc agcgttgagt tagcacgcac ttatttcact gagcgcctgc gagagcgccg    900
aggggttatt gagactagcg ataagctgga agtccgacct gcggggggcca accgtaccgc    960 cactcacggg gcgtcttgaa cgtccgtacc ccgactccgc agattaagtg cactagttag  1020
ttaa                                                               1024

<210> SEQ ID NO 3
<211> LENGTH: 1195
<212> TYPE: DNA
<213> ORGANISM: Artificial
<220> FEATURE:
<223> OTHER INFORMATION: DNA sequence of an Intergenic Sequence Region
      or ISR, ISR2.
```

<400> SEQUENCE: 3

```
aacgtaatcg tatcgatcgt ttactagatc tggcaccgaa aggaccgcca agctcagttc    60
ttgaattgtg ataccccgc tcctagccca gtacgggttt cgagacacgt cagatccttt   120
aacggcaaat ataatcggtt actgaactgc tgtctattgg ggatatcgac actcaatcac   180
cgcacgcggg atcaacctat ttggctgctg agttgtcgca cgggtctctc ccttcctctt   240
atagcgagga ttgtatcgct cctttttgccg gtgctttacg aaagaccttg cagctgttaa   300
gacttcttcg tgatagggtc ccctaaaaga agactatctt gtttccgttc ccccaactca   360
gtaaacgagg cactcaccag gaggcaggtt gtacgtcaac gttagcgcgt cttagggggca   420
gactttacgg taacttctcc gcaccctggt cacgtcctgg gcctaaagga aagcccgccc   480
aacgggcctt taaatccgag tccaaggaaa actctgggta cagatacaga ctttaagtaa   540
agcttcgatc actccttgaa tacggaggat acgaactgtc cgccttattg aagagaggtg   600
gcagcgaggt atccgacttt ggcgccggct accgtatcaa gaaggccgcc tttaggatag   660
agataacagc ggtcttaatt aggcgggcct tgaggtgctt ggcagtaacg gcagagcgaa   720
agcctccccg tcgtgattta gtctttggaa ggtcaggtcg aaagccgaat atcggtagca   780
ctatcgagaa taagggtgtga agtatacaca cttctctgtg ctttagcaat cagtataatc   840
gtagctacgt taccccagaa gccagagatc ccctccttg agctagaggc ggacgcaagc   900
tgagcgcctt acgccgcgtg ggcaatacgg cagaaggcaa aatttcaacg acttgctaga   960
aaagcagttt gaaggagcct aacagcttca cagaggctca atacctcgta ggtatcggtg  1020
cttagcgccg atctgcgtac gagccttgta tcgtcgttcc ctaatcggag tattcgggga  1080
cttggagtgg cagagttcgc aacccttact acaccgtgtt gactgacaaa aagcacggtt  1140
cagtgaggcg gtttagttcc gcttgagcgc ttggagcgta tccctcaaat cgaag        1195
```

<210> SEQ ID NO 4
<211> LENGTH: 1195
<212> TYPE: DNA
<213> ORGANISM: Artificial
<220> FEATURE:
<223> OTHER INFORMATION: DNA sequence of an Intergenic Sequence Region
      or ISR, ISR4.

<400> SEQUENCE: 4

```
cgtcagcccc tccaaggtgg atcaagactg caccggcaag cagtgtagtc tctctttcta    60
gatttggcaa agtcacttgt cggagcggtg tgatcgcacg ctttagcgcg gcgagagcgt   120
cctcgcgagt tatccccagg ctcgccaagg cccgtgttgc gcgtatcaag aatcttagag   180
ttcgactgct gttcacagag gagctaagga gattggaccg tgccgctgaa cagccagatc   240
caccgggggc tccggaccta agctgctaaa gatttcgcaa gcggaatccg ccaaatctat   300
acagatccga accagacagg cgactacgcc gttgatcagg ggtgaagtta cttactatcg   360
gatctatcgt cgcaaggaga gacggtttct ggaaacggcc cactcacgtc tgctggtcta   420
cacgggtctt aaatatcgga tagaatcgct tatccgcggc ttctagcaag cagagagaac   480
aacgtcttct ttcgcgcccg tgcgacttca ataaattgcg agcaattgcc cgtagcccaa   540
aaataaaaat cgatcaggct accagaacga tcaggcaggt acttatattg taatcaaggg   600
aaattttaac gagttccgac aaggtggaag ccagattgta tcacttaagg cttctgcttc   660
caactactta ccctcaccac cacttacgct tcacctcaag aagtaacttc gtggttctgt   720
acgccggaga gctgctcggt aattaacgac taggaccagc ggagccttag ctttagagat   780
```

```
cacttgaact acaccacttt cgactgggaa gtagcaggca gccttctctc cgcgggtaac      840
gtcgaatctg ctgatcggcg tgcagctggc cttaaatctg aactcgtccg ccttttctg       900 ttgaccaaga gtggaaaaag tggcccgctc tttttaaatc agcgtgactt cgcgaaactc      960
cttcgttctg tgaagggtgt ggcttttgct tagacctaac gctcgccgtg gtacgcttcg     1020
gaacacctgc ggggtcgatt cgatctccag gtcgagttca gctcagtaaa ggtttatatc     1080
accgtaaagt ctgagccgtc cgactgagca caaattaaca cagtattacg acagggagta     1140
ttacaataga tttgcagcgc gggaccctct cagatcaacg gttgtacacg ataat          1195

<210> SEQ ID NO 5
<211> LENGTH: 3024
<212> TYPE: DNA
<213> ORGANISM: Artificial
<220> FEATURE:
<223> OTHER INFORMATION: DNA sequence of an Intergenic Sequence Region
      or ISR, ISR97.

<400> SEQUENCE: 5
ctagctagct aaatcaaagc cgtaaggttt ggcgccgaca attgtgcggc agctggccgc       60
agaggggacg cgcgaaggga caccacgtaa gtcaaggacc cggcaagttc agtgaggcgt      120
caagcttctg gagagttgtt ttcacgtaag cgttgcggag ccggcctcag ttgccagcgt      180
tgaggacgcc accggaaatc gcctggaaat cggcgcgtgt atcactgaaa ggctagcctc      240
aggcggtact taaatcgccc ccgagcttcg gtccacgggg tgttcttcac gtacggggtt      300
cagacctcag cgtggtccac gggccaggga cgttaagcta tcccggtcct aggcggaagg      360
gacggttccg cctcaattga aggcgaggcc gcacggttga ccgacggccc cccagattga      420
caggcttcgt ctaaactttg cgacttcctc gagccctgtc agttgtagca gaggcaggct      480
ctgtcgttgg tcctccctac cggacgggct ccggcttcac ggtgagtaac tggaaacggt      540
ggggggggcc tcgatagatc gtaccagacg ttacagtgga tcttcgcaca ctactgattc      600
agtgaagtac gttccgcccc ggctggtcgc gtacgatctt tgacgtcagc actagagccc      660
aagcttgaag ggcgacgtgc gtctggtatt tagggctgtg ttggggtgct ctggagcaag      720
gaggtcacaa agagatcttc cagggtccta cgccgggtta gccgcgttgc taactctaat      780
tggcgagccc cccgagaggt gtttatagct gaatatcagc agtcggccgc caactgaacc      840
agactactgc gaaattttta agtccttaga tcagcgaaca gccaacgctc cgttgggcac      900
agccccttgt ccggtagtgc cctcacctag caggcgcccc gtgaccccctt ggcgataacg      960 aacagctgcc cacaccgtcg tagacctttc tcactggccg ccacctgaac ctagcttctg     1020
cgagtggctc tgtgctctag acctctcgca cgtttaaccc ggcagtgtgg cagaaggctc     1080
ggctaccagc tagcggtgat ttgggtaacc gacgtacagc acgtcagaca ccacggataa     1140
gccccaaata atatccaagg ggcggccaat cgccgcgaac ttactcccta ccgcctgagc     1200
ctggtcggtt gcacggacgc gaagacacta cgcgcctacc cgcaacgtgg caactacagc     1260
gagtgtcaat aatagtgcgg gccgcgggag ttcgtgtata ttaagcggac cccctcttc     1320 tagtgcacac ccctagccac tcagggcgga cgccgcctgc cggatacgt ctaccaccgc     1380 gtgttcgccc ctctaacacc acctagaact tgccggagag ggaggggggtc cagggagtga     1440 cgaagtcaac accactcctc ttgtctccgt cccttggctc cagcgaccga gtcgattgga     1500
aggttagagg gtagtgcgga tcccgtgctt tgaacggccg acgccctcac gatactctag     1560
cctagaccaa cctacggctg ctcaggcgct tgggcagtgg ccgtgggtcc gatcggccaa     1620
```

| | |
|---|---|
| agggatagc ctccaggcgg tcttcccccc ttgactgtgt tcgcgcgctc tacgacgtag | 1680 |
| acgcaatcta ctggtccctg gcgctgcgag gctagttcca gaaactactg tttacaaata | 1740 |
| gggtccctcc tgtcgatcgt agcttgacga cgcctctgcc gcccgtagcg tactggaagg | 1800 |
| agggagtgct agagtaaccg tggcggcgtg cctagcgaat cccgattcga gcgcgacccg | 1860 |
| gttgtgtgaa aaagactaag atcgggactt agcacgtatc agtaggtttc tacccgaagt | 1920 |
| gccgttttac cacgcaggga acttggcggt atccccgctc cttgcacacg tcgtctagcc | 1980 |
| tagctgcggt tcgttctcag ggctgggccg tttaatcttg cgcggagggg actcctggat | 2040 |
| ccaggggtc ggcggcaagg gggcaccaga tccgaagatc tagacggccg tcggtagcgt | 2100 |
| aattacgcag gggatccgtc agttggtagt cctagataac acttgttggg gtggcgtagt | 2160 |
| tctggccccg gttcctgacg tgcaaagttt acccgcccgg ggccgaccac gttttataca | 2220 |
| ggcgtttgtt gtttagtgca atcctatcca ggatccgctc ccgcgttcgg ctacaggcac | 2280 |
| cccacagtta aacggcacct gtgttagacc ttgggcggcg gcgctctacg gcgacccgtg | 2340 |
| ctacaagggt tagcggtcgc gctccgacga tccggtggct caagagacga gggcagcgtg | 2400 |
| tgtgaaagag tcactagtgg tggccccgcg acttaaacgt ccgcacaggt ggatcctaaa | 2460 |
| tcttacgcgg cccgccccga cctagccctg gttcgggaga gtgtactttg attgcaagca | 2520 |
| gggcgccacg tcagatcgtc ctgtagcctc gcccttatcg caattttgag tgcacggtta | 2580 |
| ggcccccgga gaatcaccta ataccccgaa agagccctgt gaccgcttgg ccaccgtcgt | 2640 |
| agaactggga tccgacgcac gggcgaaagc gagggaggat acactgtcgg gggtaagacc | 2700 |
| cacctaaact aacacccgct caccgctgtt tcgtgccccc gactcttgcc tggacgcaat | 2760 |
| aactgggacc gggagtcaaa ctcttactcg ggacggtcga ccgcgtaggc ggacagcaca | 2820 |
| gtaacagtta ggctagctga cagagcaagc agccgaactg gtaagacctt gctctattcg | 2880 |
| gagcctggac ctggctgttg cggtgtgtgt caccgggtgt aacagtaacg gagtctcaag | 2940 |
| ggcgacctgc taaaggtcta tctacgcggt aagcgggttt ctgtcggtta agcgcagcac | 3000 |
| cgcttgttct agttagttag ttag | 3024 |

<210> SEQ ID NO 6
<211> LENGTH: 1035
<212> TYPE: DNA
<213> ORGANISM: Artificial
<220> FEATURE:
<223> OTHER INFORMATION: DNA sequence of an Intergenic Sequence Region
or ISR, ISR69.

<400> SEQUENCE: 6

| | |
|---|---|
| cgcgccttag ttagctaggt ggttcgtagt ttaagcactc ctagtggact gattattccg | 60 |
| tcctttcaga cggtcagcct taccgagagg cctctccaaa tagcagacac agtatatacg | 120 |
| ttaaaaagac cgcgtagtgg tgctgcctga caggcgaagg tcaaagggac ggcccctatc | 180 |
| gattataaaa gccctcagtg cacgaggcgg aggtacaagg tcccacagtt gtcgtcccct | 240 |
| gcagcctctt ggacgcctag cgcctcgtga tagctagcag ctgaggggtt acgggccgtg | 300 |
| atattccgac tataccacta gtctgcggcc tctgatcacg ccttgctgca atctatcggt | 360 |
| taaaccagag cttctttgct cactgagggg atacctcaaa tacctaaaag atcccagtgg | 420 |
| aggtggttag ttctgcacaa gataccgata cgccggttct tgccctcgcg tcgctaatcc | 480 |
| caaattagga tcaggggattg agtttggccg ccgggtcctc gtgaacaggg atcgtcgttt | 540 |
| ccttcaggga agccaccctg atttactctg gggggccgat tagggtgacg ctcgccacca | 600 |

| | |
|---|---|
| atagcgtacc gggagtgctc tcactttccc gcacaagcac actggttacg atctagccta | 660 |
| cggagtcgct cctttcaag tgggagggtg cttcttcttt aaccgcgact aacgaagctc | 720 |
| agcttgttgt ttcacccggt ttacttccca gtaccagtat ttaatagctt agagttgaat | 780 |
| ctcaattaaa agtcagggga ggaacctcac gagaaggacg attacacgtg aagctagtac | 840 |
| gcgcgataca cgtagttcac gctagatcgt tgtatagacg caatataccg gaccttacac | 900 |
| tcttttccc tgagtgctaa aagaccgcag tctaatctcc actcgaatcc aaagcggtca | 960 |
| ggtggctaag tggcctcgat cggtggacag gagtaaagca ctgtcgatca cagtgctgtt | 1020 |
| agctaactag ggtac | 1035 |

```
<210> SEQ ID NO 7
<211> LENGTH: 1024
<212> TYPE: DNA
<213> ORGANISM: Artificial
<220> FEATURE:
<223> OTHER INFORMATION: DNA sequence of an Intergenic Sequence Region
      or ISR, ISR88.

<400> SEQUENCE: 7
```

| | |
|---|---|
| ttagctagtt aatccgggcc ctgattcgcc cctagtgctc ctcaaactct tcaaagaggg | 60 |
| ctgcgagggt ggtatacttt ggtagcaaca gggtgcttgg gcagcaaggt cccctagga | 120 |
| gaggttcctt tgataatag atttaggac tttacgcgcg cgcaattccg cgcaggcttg | 180 |
| cgggcactaa acgccgtacc gtgggctcgc gcggggtagc gggtgggcgc tgatcacggt | 240 |
| aagacttgcc gggtgatacc gggcaagagg ttcagagaag atacgttttc ctccctcagg | 300 |
| acaaatattc ttgcccacca gctgcggacg ggcctgctac tccgaaggac ctaggacgtc | 360 |
| gtgtagtaca ggggctccgt ttgtccctgt aggttcaagt ccttagtgcg gaaggtggtg | 420 |
| gcgaaggagt gccgtttcgg ggctgctggc tgaggtggag ttggtgtgcg cccgttaata | 480 |
| ccccggccga ctgactactg gtagggacaa ttcgcaaacg gacgcactac tactaacacg | 540 |
| gaggcagagc gaccaccgtg agggtccaca cccgagggct cgttcgacta cgcacgtcac | 600 |
| agagacggac gctcgggctc ggcctcaata gcgctgtgca gcgtacagcc ctctgtttaa | 660 |
| tacaggccta acgcgtcaag accggaaccc cttcgacta ctgtgaagag cgccttcggg | 720 |
| cccccgtttg gccacaactt cacaaccgcc ccctgacgga atactaattc gcttggtccc | 780 |
| taaaggctag cgagcccaag gacctatcac taggggacgg cgctcgtggc cttagattcc | 840 |
| ctgaggcgcc ccttcctcag cgagtcggcc tgtgtcggtc ccccgattcg agtaaccacg | 900 |
| caaggcgtac aagcgcctaa cttgagccgc tcaccgaggt ccttaagacc ctagaaacgg | 960 |
| cttcccaaac ctgcgtctta agtctgacgc ccctagcgga ccacgacggc agttagctag | 1020 |
| ctag | 1024 |

```
<210> SEQ ID NO 8
<211> LENGTH: 1024
<212> TYPE: DNA
<213> ORGANISM: Artificial
<220> FEATURE:
<223> OTHER INFORMATION: DNA sequence of an Intergenic Sequence Region
      or ISR, ISR86.

<400> SEQUENCE: 8
```

| | |
|---|---|
| ttaactaact aatagcaaac ccccgcacca gcaaacttag aggaaacagt caacggatct | 60 |
| aggcacaaaa aactcagatc gacagaggga atcgaggcga atcgtagtgg actagtgcta | 120 |

| | |
|---|---|
| ctgtctgtat acaaggatta tttgtgctct gggtgaagcg ttccgcgttt ccttcggcgg | 180 |
| ttgagaggcg ggaatcccga taaacgctga gattaagata gccctagtag gggatcgtcg | 240 |
| tcacgttatc gaaccgcccg gtccctctat ttcttcactg cctagccggt agttcgaagt | 300 |
| gacccttact tgcccagaga taataagctc tgctgggcct tcttattgca atcaggcgta | 360 |
| attgtgtatc cgtcccacgc aactatattt aaacgtgacg tccctcccta gaaagtaagg | 420 |
| cctacgattt tatcccgaac gggtcggatt ggggaaggtg cgcttttggt ctaccttctg | 480 |
| ggatcactat caccttggtc cgtacccgta agcgctgctt tgtatttag tacggcgcta | 540 |
| tagaccgcta taagaatcgc tctgcttccc ccaagtcaac taaactagac gaaaggatca | 600 |
| gctgggtaat cctggacgtc taggatcttt gttcgttcaa gtattacgca gggcggatcc | 660 |
| acagtacctg taaacaaggc cgttccgtcc ctaagccgtt ttaatcctca ggctagtaca | 720 |
| ggcacgttac tgctgtagtt ttgggtgtgc cgcgacgag aacagtccgc acgggtagcg | 780 |
| ctgcggcgcg ggacgagttt aacctactgt gcaatcgcag tgcagtgccg tagcactatc | 840 |
| gtccgttaga accacagtaa gtcaaactag ccttccgagg ttcaccactc gtggctttca | 900 |
| ggcaccaaac cggtagaatt tttgccagcg agccgctaaa gaatccactc aagccagatt | 960 |
| aaaaattata attcgaggag gccagtgtac gtggactccg tggtattagg tgttagctag | 1020 |
| ctaa | 1024 |

<210> SEQ ID NO 9
<211> LENGTH: 1219
<212> TYPE: DNA
<213> ORGANISM: Artificial
<220> FEATURE:
<223> OTHER INFORMATION: DNA sequence of an Intergenic Sequence Region or ISR, ISR_X.

<400> SEQUENCE: 9

| | |
|---|---|
| ttagttagtt agcgtaaggc ccgcccaggt ggtgctagac tccgccccta gcaagtgttc | 60 |
| gctgtcttgc tagttttggc gacgtgactt ctctgagcgg agctatctta cgaaaaacgc | 120 |
| cgccctgagt gtgctcacag gatagctcca cggaggagaa cgctcgtgta ccgctttaga | 180 |
| tcactctgag ggagtgtctc ctagtgacac gggagcttag cggaaccctg cgagccccag | 240 |
| atcagaaaga ttcaccgcga gctctgatcg ttaggtgcta aaggaatcgc aagcccaatc | 300 |
| ccgcaatcct attcaaatcc aaaggaggca caagacccca ccctagattt gaggtaaagt | 360 |
| tcgtaacgat ctgatatctt gccgcaagga gtggttctgt ttggtaatcg aatcctcaag | 420 |
| tcttcagttc acctcaggtc ttaagtctcg tcttgattag gctgtccgtc gtcccgaaca | 480 |
| aggacggtat acccgttctt gtataggtac agtccgcctc actaaaattg cctgtaattg | 540 |
| cgaataacgg aataattaaa atagatcacg ctaaggaaac gctcacaccg gtccttctat | 600 |
| tggagtctcg gtgattttg gcgtccgcgg acaacctact agccagttag ttccccgtaa | 660 |
| cgataccgtg tcctaggagt tagcctgggc agcctttacc ctttaccacc tgaggcttct | 720 |
| taagactaca gattgtctcg aagctgatcg gttctaatcg accaatacta ccggagcgtc | 780 |
| ggttggacag atcacctcca gaacacctct accctctggc tcccagcagg tagcttagtg | 840 |
| cccacgggtt aagtgtaaat tgcttatcgg cgtggtgctg gcctgtaacc tgtccaagac | 900 |
| ctcgcgtatc cgaacactaa gcgtgtaaaa agtgcggcgt tgctgatata tcaaagcaac | 960 |
| ttggcgtagc gccttcgttc agtaaaggca gtccctgttt cttcgaggac tccaccgaaa | 1020 |
| gcgcgcgcta cggagctaga gcggcgtagg atcgtaatcc acgctcagtg agcgaaagta | 1080 |

| tttgtatata gcacggtcca gccagtttag ttctacctat ccctaatcaa caccgtatt | 1140 |
| taccaccaac ccttgtcaga gtattcaaca cgtagactct cgccgatcaa cggtagtcca | 1200 |
| ccaaacttta gttagttag | 1219 |

<210> SEQ ID NO 10
<211> LENGTH: 333
<212> TYPE: DNA
<213> ORGANISM: Artificial
<220> FEATURE:
<223> OTHER INFORMATION: DNA sequence of an enhancer, E-CaMV.35S.2xA1-
      B3-1:1:1.

<400> SEQUENCE: 10

| catcgttgaa gatgcctctg ccgacagtgg tcccaaagat ggaccccac ccacgaggag | 60 |
| catcgtggaa aaagaagacg ttccaaccac gtcttcaaag caagtggatt gatgtgatat | 120 |
| ctccactgac gtaagggatg acgcacaatc ccactatcct tcgaggcctc atcgttgaag | 180 |
| atgcctctgc cgacagtggt cccaaagatg accccacc cacgaggagc atcgtggaaa | 240 |
| aagaagacgt tccaaccacg tcttcaaagc aagtggattg atgtgatatc tccactgacg | 300 |
| taagggatga cgcacaatcc cactatcctt cga | 333 |

<210> SEQ ID NO 11
<211> LENGTH: 840
<212> TYPE: DNA
<213> ORGANISM: Oryza sativa
<220> FEATURE:
<221> NAME/KEY: misc_feature
<222> LOCATION: (1)..(840)
<223> OTHER INFORMATION: DNA sequence of a promoter, P-Os.Act1:67.

<400> SEQUENCE: 11

| tcgaggtcat tcatatgctt gagaagagag tcgggatagt ccaaaataaa acaaaggtaa | 60 |
| gattacctgg tcaaaagtga aaacatcagt taaaggtgg tataaagtaa aatatcggta | 120 |
| ataaaaggtg gcccaaagtg aaatttactc ttttctacta ttataaaaat tgaggatgtt | 180 |
| tttgtcggta ctttgatacg tcattttgt atgaattggt ttttaagttt attcgctttt | 240 |
| ggaaatgcat atctgtattt gagtcgggtt ttaagttcgt ttgcttttgt aaatacagag | 300 |
| ggatttgtat aagaaatatc tttagaaaaa cccatatgct aatttgacat aattttgag | 360 |
| aaaaatatat attcaggcga attctcacaa tgaacaataa taagattaaa atagctttcc | 420 |
| cccgttgcag cgcatgggta ttttttctag taaaaataaa agataaactt agactcaaaa | 480 |
| catttacaaa aacaacccct aaagttccta agcccaaag tgctatccac gatccatagc | 540 |
| aagcccagcc caacccaacc caacccaacc caccccagtc cagccaactg acaatagtc | 600 |
| tccacacccc cccactatca ccgtgagttg tccgcacgca ccgcacgtct cgcagccaaa | 660 |
| aaaaaagaa agaaaaaaaa gaaaaagaaa aaacagcagg tgggtccggg tcgtggggc | 720 |
| cggaaacgcg aggaggatcg cgagccagcc acgaggccgg ccctccctcc gcttccaaag | 780 |
| aaacgccccc catcgccact atatacatac cccccctct cctcccatcc ccaccct | 840 |

<210> SEQ ID NO 12
<211> LENGTH: 61
<212> TYPE: DNA
<213> ORGANISM: Triticum aestivum
<220> FEATURE:
<221> NAME/KEY: misc_feature
<222> LOCATION: (1)..(61)
<223> OTHER INFORMATION: DNA sequence of a leader or 5' UTR,
      L-Ta.Lhcb1:1.

<400> SEQUENCE: 12

```
aaccatcttc cacacactca agccacacta ttggagaaca cacagggaca acacaccata    60
a                                                                   61
```

<210> SEQ ID NO 13
<211> LENGTH: 480
<212> TYPE: DNA
<213> ORGANISM: Oryza sativa
<220> FEATURE:
<221> NAME/KEY: misc_feature
<222> LOCATION: (1)..(480)
<223> OTHER INFORMATION: DNA sequence of an intron, I-Os.Act1-1:1:19.

<400> SEQUENCE: 13

```
ccgccgccgc cggtaaccac cccgcccctc tcctctttct ttctccgttt tttttccgt    60
ctcggtctcg atctttggcc ttggtagttt gggtgggcga gaggcggctt cgtgcgcgcc   120
cagatcggtg cgcgggaggg gcgggatctc gcggctgggg ctctcgccgg cgtggatccg   180
gcccggatct cgcggggaat ggggctctcg gatgtagatc tgcgatccgc cgttgttggg   240
ggagatgatg gggggtttaa aatttccgcc gtgctaaaca agatcaggaa gaggggaaaa   300
gggcactatg gtttatattt ttatatattt ctgctgcttc gtcaggctta gatgtgctag   360
atctttcttt cttcttttg tgggtagaat ttgaatccct cagcattgtt catcggtagt    420
tttctttttc atgatttgtg acaaatgcag cctcgtgcgg agctttttg taggtagaag    480
```

<210> SEQ ID NO 14
<211> LENGTH: 795
<212> TYPE: DNA
<213> ORGANISM: Escherichia coli
<220> FEATURE:
<221> NAME/KEY: misc_feature
<222> LOCATION: (1)..(795)
<223> OTHER INFORMATION: DNA sequence encoding neomycin
      phosphotransferase, CR-Ec.nptII-Tn5-1:1:3.

<400> SEQUENCE: 14

```
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcaggggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg catgcccgac   540
ggcgaggatc tcgtcgtgac gcatggcgat gcctgcttgc cgaatatcat ggtggaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
gacgagttct tctga                                                   795
```

<210> SEQ ID NO 15
<211> LENGTH: 210

```
<212> TYPE: DNA
<213> ORGANISM: Triticum aestivum
<220> FEATURE:
<221> NAME/KEY: misc_feature
<222> LOCATION: (1)..(210)
<223> OTHER INFORMATION: DNA sequence of a 3' UTR, T-Ta.Hsp17-1:1:1.

<400> SEQUENCE: 15
ctgcatgcgt ttggacgtat gctcattcag gttggagcca atttggttga tgtgtgtgcg      60
agttcttgcg agtctgatga gacatctctg tattgtgttt ctttccccag tgttttctgt     120
acttgtgtaa tcggctaatc gccaacagat tcggcgatga ataaatgaga ataaattgt     180 tctgattttg agtgcaaaaa aaaaggaatt                                      210

<210> SEQ ID NO 16
<211> LENGTH: 1456
<212> TYPE: DNA
<213> ORGANISM: Zea mays
<220> FEATURE:
<221> NAME/KEY: misc_feature
<222> LOCATION: (1)..(1456)
<223> OTHER INFORMATION: DNA sequence of a promoter, P-Zm.39486-1:1:1.

<400> SEQUENCE: 16
tgtttggact ccagaaaatt tacgggagtt ggtggagcag gtcattaagt actataaaaa      60
atcatgtagc tgaagctgca agtatttaga agacatttag ataagttatt ttatttatca    120
tttagattaa gaaaatttaa aactatttaa attgatatta taaactacag ctccacactg    180
gagctagatc ctggagtcat tacaaacacc cccttaatgg gaaagagaaa gataatgtat    240
atctaattat tgtttctgtg tcacctatag ctattagttc aaaacttcat aatcactggt    300
acaaataagc tctagagagg cggttcggaa cccatttttta ttgttgtttt tcaaaaccac   360
tagtgttagg gaccgccagt ggaaactgaa acgccattgg aaattgattt tcactgatgg    420
tgagctaaga aaaccgccat tggtaatcct ttgcagaaaa cataaactag gttttaaaaa    480
tagtaaacaa atatttttat taggagaggc cccacatagt cgcaccattt ttcgcgcatt    540
attcacgcgc tacgcaacca atggtaattg aacctcagag acttcactct tgtgtagcct    600
cctttgccac tccactaaac acttacttgt gtcttgattg cattttgttg cccacatatt    660
agaacaaaca gagtgtaaat tgattgtttg aggctgtaaa caaattcaaa tgaaaaagta    720
gtcaactact aaattgaata attgtttatg ttctaccact tttatttttgg tacttttccc    780 atcggaggcg gtttgtaaaa tttgcatttt aagttttaca aatttcaatg aaattttgag    840
agcccaaatg atttcaaata aaaagttgt caactacaat gttttataac ttttaatttg     900
gtggtttttt aaacaagctc atttgaaaaa ctaaatgat cgattctaca tgattttttag    960 gtcgatttt taaggaatcg cctgtacaaa tatttctact gacagttttt aagaaaccac    1020
ctgtggaaat catagatttg tactagcggt ttttctcaag taactgctag tagaaatatg   1080
gtggttttct taagaaaact gttttgtagga atgcacgatt tatataaatg gatttgttaa  1140
gaaaaccgct agtggaatgt tctttcaact aacggttatt gagtcgtgac agccaattta   1200
atttccttga taactaaaag cggctgtaaa aattagacca tgatgtaggc acggagctgt   1260
tttgtactga atgcgcccac tgtttttgttg gaaaagtgca tgtacttatt attcattctg  1320
tttatttcta gctggcattc agttcttaca gccacagatt atgcaaaacg cctatttctg   1380
ccagcaaatt tacaggaaaa gtcatggact tttccgggtt attttcctat aagtacagcc   1440
attcctttca cttaca                                                    1456
```

<210> SEQ ID NO 17
<211> LENGTH: 46
<212> TYPE: DNA
<213> ORGANISM: Zea mays
<220> FEATURE:
<221> NAME/KEY: misc_feature
<222> LOCATION: (1)..(46)
<223> OTHER INFORMATION: DNA sequence of a leader or 5' UTR, L-
      Zm.39486-1:1:1.

<400> SEQUENCE: 17

```
ggccccaaca ttagcacaaa gaacacaata gaccactgat ttaaca              46
```

<210> SEQ ID NO 18
<211> LENGTH: 804
<212> TYPE: DNA
<213> ORGANISM: Zea mays
<220> FEATURE:
<221> NAME/KEY: misc_feature
<222> LOCATION: (1)..(804)
<223> OTHER INFORMATION: DNA sequence of an intron, I-Zm.DnaK:1.

<400> SEQUENCE: 18

```
accgtcttcg gtacgcgctc actccgccct ctgcctttgt tactgccacg tttctctgaa    60
tgctctcttg tgtggtgatt gctgagagtg gtttagctgg atctagaatt acactctgaa   120
atcgtgttct gcctgtgctg attacttgcc gtcctttgta gcagcaaaat atagggacat   180
ggtagtacga aacgaagata gaacctacac agcaatacga gaaatgtgta atttggtgct   240
tagcggtatt tatttaagca catgttggtg ttatagggca cttggattca gaagtttgct   300
gttaatttag gcacaggctt catactacat gggtcaatag tatagggatt catattatag   360
gcgatactat aataatttgt tcgtctgcag agcttattat ttgccaaaat tagatattcc   420
tattctgttt ttgtttgtgt gctgttaaat tgttaacgcc tgaaggaata aatataaatg   480
acgaaatttt gatgtttatc tctgctcctt tattgtgacc ataagtcaag atcagatgca   540
cttgttttaa atattgttgt ctgaagaaat aagtactgac agtattttga tgcattgatc   600
tgcttgtttg ttgtaacaaa atttaaaaat aaagagtttc cttttgttg ctctccttac    660 ctcctgatgg tatctagtat ctaccaactg acactatatt gcttctcttt acatacgtat   720
cttgctcgat gccttctccc tagtgttgac cagtgttact cacatagtct ttgctcattt   780
cattgtaatg cagataccaa gcgg                                           804
```

<210> SEQ ID NO 19
<211> LENGTH: 2001
<212> TYPE: DNA
<213> ORGANISM: Artificial
<220> FEATURE:
<223> OTHER INFORMATION: DNA sequence of synthetic coding sequence
      optimized for plant expression for beta-glucuronidase, GUS-1:
      GOI-Ec.uidA+St.LS1.nno:1.

<400> SEQUENCE: 19

```
atggtgaggc ccgttgagac cccgactagg gagatcaaga agctggacgg cctctgggcc    60 ttctcccctcg accgtgagaa ctgcggcatc gaccagcgct ggtgggagtc cgccctccag   120
gagtctaggg ccatcgccgt gcccggttcc ttcaacgacc agttcgccga cgccgacatc   180
cgcaactacg cgggcaacgt ctggtatcag cgcgaggtgt tcatcccgaa gggctgggcg   240
ggccagcgca tcgtgctccg cttcgacgcc gtgacccact acggcaaggt ctgggtgaac   300
aatcaggagg taagtttctg cttctacctt tgatatatat ataataatta tcattaatta   360
```

```
gtagtaatat aatatttcaa atattttttt caaaataaaa gaatgtagta tatagcaatt      420
gcttttctgt agtttataag tgtgtatatt ttaatttata acttttctaa tatatgacca      480
aaatttgttg atgtgcaggt gatggagcac cagggcggtt acaccccgtt cgaggccgac      540
gtgacgccgt acgtgatcgc cgggaagtcc gtccgcatca ccgtctgcgt gaacaatgag      600
ctgaactggc agaccatccc gcctggcatg gtcatcaccg acgagaacgg caagaagaag      660
cagtcctact ccacgactt cttcaactac gctggcatcc accgctccgt gatgctctac       720
accactccca acacctgggt ggacgacatc accgtggtca cccacgtggc ccaggactgc      780
aaccacgcct ccgtggactg gcaagtcgtt gccaacggcg acgtcagcgt cgagctgcgc      840
gacgccgacc agcaagtcgt tgccaccggc cagggcacca gcggcaccct ccaagtcgtc      900
aaccctcacc tctggcagcc tggcgagggc tacctctacg agctgtgcgt caccgccaag      960
agccagactg agtgcgacat ctaccctctc cgcgtcggca tcaggagcgt cgctgtcaag     1020
ggcgagcagt tcctcatcaa ccacaagcct ttctacttca ctggtttcgg ccgccacgag     1080
gacgctgacc tgaggggcaa gggtttcgac aacgtcctga tggtccacga ccacgctctg     1140
atggactgga tcggtgccaa cagctacagg accagtcact acccgtacgc tgaggagatg     1200
ctggactggg ctgacgagca cggtatcgtc gtgatcgacg agactgctgc ggtcggtttc     1260
aacctgtctc tgggcattgg tttcgaggct gggaacaagc cgaaggagct gtactctgag     1320
gaagctgtca acgcgagac tcagcaagct catctccagg cgattaagga gctgattgcc     1380
agggacaaga accatccgtc tgtcgtgatg tggtctattg cgaatgagcc ggacaccaga     1440
ccgcaagggg cgcgtgaata cttcgcgccg ctggcgaggg cgactcgcaa actggaccca     1500
acccgtccaa tcacgtgcgt caatgtcatg ttctgcgacg cccatacgga tacgatctcg     1560
gacctgttcg atgttctttg tctcaatcgg tactatgggg gtatgttca gagcggggat      1620 cttgagacgg cggagaaggt tcttgagaag gaactcctgg cgtggcaaga gaagctccat     1680
cagccgatca ttatcacgga gtacggggtt gacacacttg cgggccttca cagtatgtac     1740
acagatatgt ggtcggagga ataccagtgt gcatggttgg atatgtacca tcgtgtcttc     1800
gaccgggttt cagcggttgt cggcgaacaa gtctggaact tcgcagactt cgccacgagc     1860
caagggatac tgcgggtagg agggaacaag aagggaatct tcacacggga tcggaagccc     1920
aagtcagcag ccttcctgtt gcagaagcga tggacaggaa tgaacttcgg agaaaagcca     1980
cagcaaggcg gaaagcagtg a                                               2001
```

<210> SEQ ID NO 20
<211> LENGTH: 300
<212> TYPE: DNA
<213> ORGANISM: Oryza sativa
<220> FEATURE:
<221> NAME/KEY: misc_feature
<222> LOCATION: (1)..(300)
<223> OTHER INFORMATION: DNA sequence of a 3' UTR, T-Os.Mth-1:1:1.

<400> SEQUENCE: 20

```
ggccaaggcg atctatgact gaattgccaa tgcaccagcc tgtctacatg atgaataaat       60
aaagagtcca tccagtgtga tggctcatgc ctgtgtgagt gtgactgaat ccatcagtgt      120
gtgtgtgtgt ttgtgtcaac catgtgtgaa tcaggtgtca aaaatcgtgg ctggaaatcc      180
atgtggtttc tagctttatg taaatgttgt ttgtgaaata taatattgt tttgtgtatg       240 tgaattttac tctctcattt ttctcttgca ctcaccattc tattatagta attttttaa       300
```

-continued

```
<210> SEQ ID NO 21
<211> LENGTH: 981
<212> TYPE: DNA
<213> ORGANISM: Artificial
<220> FEATURE:
<223> OTHER INFORMATION: DNA sequence of a promoter, P-FMV.35S-enh-
      1:1:2.

<400> SEQUENCE: 21
aattctcagt ccaaagcctc aacaaggtca gggtacagag tctccaaacc attagccaaa      60
agctacagga gatcaatgaa gaatcttcaa tcaaagtaaa ctactgttcc agcacatgca     120
tcatggtcag taagtttcag aaaaagacat ccaccgaaga cttaaagtta gtgggcatct     180
ttgaaagtaa tcttgtcaac atcgagcagc tggcttgtgg ggaccagaca aaaaaggaat     240
ggtgcagaat tgttaggcgc acctaccaaa agcatctttg cctttattgc aaagataaag     300
cagattcctc tagtacaagt ggggaacaaa ataacgtgga aaagagctgt cctgacagcc     360
cactcactaa tgcgtatgac gaacgcagtg acgaccacaa agaattagc ttgagctcag      420 gatttagcag cattccagat tgggttcaat caacaaggta cgagccatat cactttattc     480
aaattggtat cgccaaaacc aagaaggaac tcccatcctc aaaggtttgt aaggaagaat     540
tctcagtcca aagcctcaac aaggtcaggg tacagagtct ccaaaccatt agccaaaagc    600
tacaggagat caatgaagaa tcttcaatca agtaaacta ctgttccagc acatgcatca     660
tggtcagtaa gtttcagaaa aagacatcca ccgaagactt aaagttagtg gcatctttg    720 aaagtaatct tgtcaacatc gagcagctgg cttgtgggga ccagacaaaa aaggaatggt    780
gcagaattgt taggcgcacc taccaaaagc atctttgcct ttattgcaaa gataaagcag    840
attcctctag tacaagtggg gaacaaaata acgtggaaaa gagctgtcct gacagcccac    900
tcactaatgc gtatgacgaa cgcagtgacg accacaaaag aattccctct atataagaag    960
gcattcattc ccatttgaag g                                              981

<210> SEQ ID NO 22
<211> LENGTH: 96
<212> TYPE: DNA
<213> ORGANISM: Petunia x hybrida
<220> FEATURE:
<221> NAME/KEY: misc_feature
<222> LOCATION: (1)..(96)
<223> OTHER INFORMATION: DNA sequence of a leader or 5' UTR, L-Ph.DnaK-
      1:1:3.

<400> SEQUENCE: 22
cagaaaaatt tgctacattg tttcacaaac ttcaaatatt attcatttat ttgtcagctt      60
tcaaactctt tgtttcttgt tgttgattg agaata                                96

<210> SEQ ID NO 23
<211> LENGTH: 795
<212> TYPE: DNA
<213> ORGANISM: Escherichia coli
<220> FEATURE:
<221> NAME/KEY: misc_feature
<222> LOCATION: (1)..(795)
<223> OTHER INFORMATION: DNA sequence encoding neomycin
      phosphotransferase, CR-Ec.nptII-Tn5-1:1:2.

<400> SEQUENCE: 23
atgattgaac aagatggatt gcacgcaggt tctccggccg cttgggtgga gaggctattc      60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
```

```
caggacgagg cagcgcggct atcgtggctg gccacgacgg gcgttccttg cgcagctgtg      240
ctcgacgttg tcactgaagc gggaagggac tggctgctat tgggcgaagt gccggggcag      300
gatctcctgt catctcacct tgctcctgcc gagaaagtat ccatcatggc tgatgcaatg      360
cggcggctgc atacgcttga tccggctacc tgcccattcg accaccaagc gaaacatcgc      420
atcgagcgag cacgtactcg gatggaagcc ggtcttgtcg atcaggatga tctggacgaa      480
gagcatcagg ggctcgcgcc agccgaactg ttcgccaggc tcaaggcgcg catgcccgac      540
ggcgaggatc tcgtcgtgac ccatggcgat gcctgcttgc cgaatatcat ggtggaaaat      600
ggccgctttt ctggattcat cgactgtggc cggctgggtg tggcgaccg ctatcaggac       660 atagcgttgg ctacccgtga tattgctgaa gagcttggcg gcgaatgggc tgaccgcttc      720
ctcgtgcttt acgtatcgc cgctcccgat tcgcagcgca tcgccttcta tcgccttctt       780
gacgagttct tctga                                                       795
```

```
<210> SEQ ID NO 24
<211> LENGTH: 500
<212> TYPE: DNA
<213> ORGANISM: Medicago truncatula
<220> FEATURE:
<221> NAME/KEY: misc_feature
<222> LOCATION: (1)..(500)
<223> OTHER INFORMATION: DNA sequence of a 3' UTR, T-Mt.AC139600v16:1.

<400> SEQUENCE: 24
gcatgaataa tcaagctcat aaatttcatg gctttgaatt tgtactattt tggttactag      60
aaagtgtatt tgtgtgttta tgcagtaata aatctctaag agatatatgt ttgttatttt      120
ttataattat ccaaaaaatc gttaatgttg aaaattgatt caaaattgat attgaagttc      180
tgaaaaaatc gtggcgtgat taaaaatcca aacttttta taaaataata ttgtgtctat       240
atcttttata aatgacgata aatgggataa agtaaatgaa acaaaaccgt taatgcaatg      300
ttcatctgca caatatatat aattaaaaaa cattataaaa ccttgttttct tcactcattt     360 acaatcttga aattttagtc tttaccattt gaaagtacaa tcttttcatg aaagtttata      420
gtacaaatca agagtttgga taagctgctc tgcttttttat aatcactggg aaatgattta     480
tgacttggaa aaacaacttg                                                  500
```

```
<210> SEQ ID NO 25
<211> LENGTH: 828
<212> TYPE: DNA
<213> ORGANISM: Glycine max
<220> FEATURE:
<221> NAME/KEY: misc_feature
<222> LOCATION: (1)..(828)
<223> OTHER INFORMATION: DNA sequence of a promoter, P-Gm.Sphas1:14.

<400> SEQUENCE: 25
ggcaaaaaca tttaattcgt attatttaag aaaaaaatat gtaataatat atttatattt      60
taatatctat tcttatgtat tttttaaaaa tctattatat attgatcaac taaaatattt     120
ttatatctac acttattttg cattttttatc aatttttcttg cgtttttttgg catatttaat   180 aatgactatt ctttaataat caatcattat tcttacatgg tacatattgt tggaaccata      240
tgaagtgtcc attgcatttg actatgtgga tagtgttttg atccaggcct ccatttgccg      300
cttattaaat aaatttggtaa cagtccgtac taatcagtta cttatccttc tccatcata     360 attaatcttg gtagtctcga atgccacaac actgactagt ctcttggatc ataagaaaaa      420
```

```
gccaaggaac aaaagaagac aaaacacaat gagagtatcc tttgcatagc aatgtctaag    480
ttcataaaat tcaaacaaaa acgcaatcac acacagtgga catcacttat ccactagctg    540
atcaggatcg ccgcgtcaag aaaaaaaaac tggaccccaa aagccatgca caacaacacg    600
tactcacaaa ggtgtcaatc gagcagccca aacattcac caactcaacc catcatgagc     660
ccacacattt gttgtttcta acccaacctc aaactcgtat tctcttccgc cacctcattt    720
ttgtttattt caacacccgt caaactgcat gccaccccgt ggccaaatgt ccatgcatgt    780
taacaagacc tatgactata aatatctgca atctcggccc aggttttc               828

<210> SEQ ID NO 26
<211> LENGTH: 13
<212> TYPE: DNA
<213> ORGANISM: Glycine max
<220> FEATURE:
<221> NAME/KEY: misc_feature
<222> LOCATION: (1)..(13)
<223> OTHER INFORMATION: DNA sequence of a leader or 5' UTR,
      L-Gm.Sphas1-1:1:1.

<400> SEQUENCE: 26
atcatcaaga acc                                                      13

<210> SEQ ID NO 27
<211> LENGTH: 2001
<212> TYPE: DNA
<213> ORGANISM: Artificial
<220> FEATURE:
<223> OTHER INFORMATION: DNA sequence of synthetic coding sequence for
      beta-glucuronidase, GUS-2: GOI-GUS:1:2.

<400> SEQUENCE: 27
atggtccgtc ctgtagaaac cccaacccgt gaaatcaaaa aactcgacgg cctgtgggca    60
ttcagtctgg atcgcgaaaa ctgtggaatt gatcagcgtt ggtgggaaag cgcgttacaa    120
gaaagccggg caattgctgt gccaggcagt tttaacgatc agttcgccga tgcagatatt    180
cgtaattatg cgggcaacgt ctggtatcag cgcgaagtct ttataccgaa aggttgggca    240
ggccagcgta tcgtgctgcg tttcgatgcg gtcactcatt acggcaaagt gtgggtcaat    300
aatcaggaag tgatggagca tcagggcggc tatacgccat ttgaagccga tgtcacgccg    360
tatgttattg ccgggaaaag tgtaggtaag tttctgcttc tacctttgat atatatataa    420
taattatcat taattagtag taatataata tttcaaatat tttttttcaaa ataaaagaat    480 gtagtatata gcaattgctt ttctgtagtt tataagtgtg tatattttaa tttataactt    540
ttctaatata tgaccaaaat ttgttgatgt gcaggtatca ccgtttgtgt gaacaacgaa    600
ctgaactggc agactatccc gccgggaatg gtgattaccg acgaaaacgg caagaaaaag    660
cagtcttact tccatgattt ctttaactat gccggaatcc atcgcagcgt aatgctctac    720
accacgccga cacctgggt ggacgatatc ccgtggtga cgcatgtcgc gcaagactgt      780
aaccacgcgt ctgttgactg gcaggtggtg gccaatggta tgtcagcgt tgaactgcgt     840 gatgcggatc aacaggtggt tgcaactgga caaggcacta gcgggacttt gcaagtggtg    900
aatccgcacc tctggcaacc gggtgaaggt tatctctatg aactgtgcgt cacagccaaa    960
agccagacag agtgtgatat ctacccgctt cgcgtcggca tccggtcagt ggcagtgaag    1020
ggcgaacagt tcctgattaa ccacaaaccg ttctacttta ctggctttgg tcgtcatgaa    1080
gatgcggact gcgtggcaa aggattcgat aacgtgctga tggtgcacga ccacgcatta    1140
atggactgga ttggggccaa ctcctaccgt acctcgcatt acccttacgc tgaagagatg    1200
```

```
ctcgactggg cagatgaaca tggcatcgtg gtgattgatg aaactgctgc tgtcggcttt    1260
aacctctctt taggcattgg tttcgaagcg ggcaacaagc cgaaagaact gtacagcgaa    1320
gaggcagtca acggggaaac tcagcaagcg cacttacagg cgattaaaga gctgatagcg    1380
cgtgacaaaa accacccaag cgtggtgatg tggagtattg ccaacgaacc ggatacccgt    1440
ccgcaaggtg cacgggaata tttcgcgcca ctggcggaag caacgcgtaa actcgacccg    1500
acgcgtccga tcacctgcgt caatgtaatg ttctgcgacg ctcacaccga taccatcagc    1560
gatctctttg atgtgctgtg cctgaaccgt tattacggat ggtatgtcca agcggcgat    1620 ttggaaacgg cagagaaggt actggaaaaa gaacttctgg cctggcagga gaaactgcat    1680
cagccgatta tcatcaccga atacggcgtg gatacgttag ccgggctgca ctcaatgtac    1740
accgacatgt ggagtgaaga gtatcagtgt gcatggctgg atatgtatca ccgcgtcttt    1800
gatcgcgtca gcgccgtcgt cggtgaacag gtatggaatt cgccgatttt tgcgacctcg    1860
caaggcatat tgcgcgttgg cggtaacaag aaagggatct tcactcgcga ccgcaaaccg    1920
aagtcggcgg cttttctgct gcaaaaacgc tggactggca tgaacttcgg tgaaaaaccg    1980
cagcagggag gcaaacaatg a                                               2001

<210> SEQ ID NO 28
<211> LENGTH: 499
<212> TYPE: DNA
<213> ORGANISM: Medicago truncatula
<220> FEATURE:
<221> NAME/KEY: misc_feature
<222> LOCATION: (1)..(499)
<223> OTHER INFORMATION: DNA sequence of a 3' UTR, T-Mt.AC145767v28:3.

<400> SEQUENCE: 28
taatcatctg aaactgttca ccatgcatgc aatcttgtga aatatatggt tttaattaga     60
cttcaatctt atgttggcta ttgtactaat aaaagcatgt catgttattt tcatttgatt    120
ttatctgtac tttggtttgt ttgaagaata aagatgagct tgctatgcat gcatgcatgc    180
catcgattat cagggtttcc ttttttcttt tctggcttcc catcaatttg gtgtgaatta    240
gtgtgtgtga tatattatat tatgctattt atgaaataaa ttgttggtta tatttgatct    300
acaatctaca tacatgtgat ttttatcaac aaaatatctc gggaaacaat accttttttgg   360 tagcaaaatt caaataatac tattttaaat aaatcaaagt taaccaatac cttattcaag    420
ttggagggga ctcaaacaag caaaagaatt caagttgtta atgaacttcg gttaatgata    480
aaagaattcg catttaaaa                                                  499
```